＊

US007629139B2

(12) United States Patent
Basu et al.

(10) Patent No.: US 7,629,139 B2
(45) Date of Patent: Dec. 8, 2009

(54) EXTRACTION METHODS AND ASSAYS FOR FEED ENZYMES

(75) Inventors: Shib Sankar Basu, Research Triangle Park, NC (US); Stephanie Winslow, Research Triangle Park, NC (US); Andrea Nelson, Research Triangle Park, NC (US); Makoto Ono, Research Triangle Park, NC (US); Scott Betts, Research Triangle Park, NC (US)

(73) Assignee: AB Enzymes GmbH (DE)

( * ) Notice: Subject to any disclaimer, the term of this patent is extended or adjusted under 35 U.S.C. 154(b) by 0 days.

(21) Appl. No.: 11/455,954

(22) Filed: Jun. 20, 2006

(65) Prior Publication Data

US 2006/0286621 A1    Dec. 21, 2006

Related U.S. Application Data

(60) Provisional application No. 60/692,474, filed on Jun. 21, 2005.

(51) Int. Cl.
*C12Q 1/34* (2006.01)
*G01N 1/18* (2006.01)

(52) U.S. Cl. .......................................... 435/18; 436/178
(58) Field of Classification Search .................. None
See application file for complete search history.

(56) References Cited

U.S. PATENT DOCUMENTS 5,720,971 A    2/1998    Beauchemin et al.

2001/0055788 A1*    12/2001    Short et al. ................. 435/69.1
2005/0009116 A1*    1/2005    Yarnell et al. ................ 435/7.9

OTHER PUBLICATIONS

Augspurger et al. Efficacy of an *E. coli* Phytase Expressed in Yeast for Releasing Phytate-Bound Phosphorus in Yound Chicks and Pigs; Journal of Animal Science, vol. 81 (2003) pp. 474-483.*
Barrientos et al. Specificity of Hydrolysis of Phytic Acid by Alkaline Phytase From Lily Pollen; Plant Physiology, vol. 106 (1994) pp. 1489-1495.*
Sigma-Aldritch Bioultra Biological Buffers, 2008 downloaded Dec. 18, 2008 from: http://www.sigmaaldrich.com/life-science/metabolomics/bioultra-reagents/biological-buffers.html.*
Garrett et al., "Enhancing the Thermal Tolerance and Gastric Performance of a Microbial Phytase for Use as a Phosphate-Mobilizing Monogastric-Feed Supplement", Applied and Environmental Microbiology, May 2004, p. 3041-3046.
Engelen et al., Determination of Phytase Activity in Feed by a Colorimetric Enzymatic Method: Collaborative Interlaboratory Study, Journal of AOAC International, vol. 84. No. 3, 2001.

* cited by examiner

*Primary Examiner*—Rebecca E. Prouty
*Assistant Examiner*—Paul C. Martin
(74) *Attorney, Agent, or Firm*—Edwards Angell Palmer & Dodge LLP; Peter F. Corless; Christine C. O'Day

(57) ABSTRACT

This invention relates to methods of the detection of enzymatically active enzymes in feed added in the pre-pelleting stage. Further, this invention relates to the field of detecting thermotolerant enzymes added to feed in the pre-pelleting stage. In particular, the invention relates to the detection of a phytase enzyme, in particular an *E. coli* phytase or an *E. coli* derived phytase in feed, such as Quantum™ Phytase.

11 Claims, 12 Drawing Sheets

EXTRACTION METHODS AND ASSAYS FOR FEED ENZYMES

This application claims the benefit of the filing date of U.S. Provisional Patent Application No. 60/692,474 filed Jun. 21, 2005, which is herein incorporated by reference.

FIELD OF THE INVENTION

This invention relates to the field of enzyme assays for animal feed, and more particularly, relates to the detection of enzymatically active enzymes in feed added in the pre-pelleting stage such as thermotolerant enzymes. In particular, the invention relates to the detection of a phytase enzyme, in particular, an *E. coli* or *E. coli* derived phytase in feed, such as QUANTUM Phytase. This extraction method developed has also proved to be equally efficient in extracting phytase and other enzymes expressed in transgenic corn kernel.

BACKGROUND OF THE INVENTION

Phytase (myo-inositol hexakisphosphate phosphorylase, EC 3.1.3.8) catalyses the hydrolysis of the phosphor-ester bonds of phytate (myo-inositol hexakisphosphate). Over the last decade and a half, fungal and bacterial phytases have been successfully used as an additive in the diet of monogastric animals to improve bioavailability of phytate phosphate and other minerals. In order to measure the enzymatic activity of this animal feed additive, Engelen and colleagues published a "simple and rapid" method for measuring phytase activity (Engelen A J, et al., *Simple and rapid determination of phytase activity.* J AOAC Int'l. 77(3):760-64 (1994)). The assay conditions (37.0° and pH 5.5) prescribed by these authors were the optimal reaction conditions for *Aspergillus niger* phytase (Natuphos™), the only phytase available at that time in the market. An official version of this basic method was published in 1996 in the fourth edition of the Food Chemicals Codex (FCC). In this document, a phytase (fytase) unit (FTU) was defined as "the amount of enzyme that liberates inorganic phosphate at 1 μmol/min from sodium phytate 0.0051 mol/L at 37.0° C. at pH 5.50 under the conditions of the test."

A modified version of the FCC IV phytase method for the purpose of measuring phytase activity in animal feed was published by Engelen et al. (*Determination of phytase activity in feed by a colorimetric enzymatic method: collaborative interlaboratory study.* J. AOAC Int'l. 84:629-33 (2001)). This method was also published as AOAC Official Method 2000.12 Phytase Activity in Feed and is generally referred to as the "AOAC method." It is essentially the same as the FCC method but includes additional steps for grinding and extracting feed samples prior to enzyme assay.

The AOAC method for measuring phytase in feed, however, lacks high precision and robust reproducibility, especially for feed samples from feed batches dosed pre-pelleting with granular or particulate dry formulations of phytases and also for *Escherichia coli* (*E. coli*) derived phytases. Therefore, there was a need to adapt the AOAC in-feed phytase method for phytases added pre-pelleting and more specifically for *E. coli* derived phytases added pre-pelleting.

Traditionally, enzymes were sprayed onto the feed pellets after the pelleting step because the enzymes were not thermostable and could not survive the high temperatures used in the pelleting process, which includes steam conditioning. When the enzyme was sprayed onto the cooled feed pellets, the enzyme was distributed more evenly and only on the surface of the pellet. More recently, enzymes are being added to the mash or dry mixed feed pre-pelleting as concentrated granular or particulate dry formulations, where the enzyme is applied to a carrier or embedded in a carrier or bulking agent. The dry product particles may also be wax-coated, for example, for improved heat resistance. A key advantage to this type of concentrated dry formulation is that it can be added to feed using existing dry microingredient handling systems standard at most feed mills. A major drawback of dry concentrates added pre-pelleting, however, is that the enzyme activity is delivered not as a uniform spray but in a concentrated particulate form and at an extremely low inclusion rate. This creates new challenges relating to uniform product distribution throughout the feed batch (mixing) that has implications for both enzyme delivery to animals (i.e., uniform dosing) as well as the reproducibility of analytical methods (i.e., enzyme assay reproducibility from sub-sample to sub-sample).

New thermostable enzymes are being used in animal feed (Garrett et al., Applied and Environmental Microbiology 70(5): 3041-3046 (2004)). The new thermostable enzymes can be added pre-pelleting since they can withstand the high temperatures used in the steam conditioning and pelleting process. Using traditional in-feed analytical methods did not allow for reliable or reproducible measurements of the enzyme activity of the feed samples. The enzyme activities measured were highly variable between assays of sub-samples of the same feed samples. Possible factors contributing to this variability include a) non-uniform distribution of dry product particles, especially in samples of mash feed batches due to settling of product in stored samples, b) non-representative batch samples and sub-samples resulting from insufficient sample size, c) inefficient extraction of enzyme from granulated dry product particles in which the enzyme is embedded in the carrier or bulking agent or trapped in the feed matrix as a result for example of starch gelatinization, and d) low signal-to-noise ratio in activity assay due to sub-optimal assay conditions.

Dry formulated enzymes are typically added to feed at very low inclusion rates, resulting in extremely low concentrations of enzyme in the complex mixture of the feed. For example, the recommended dose of QUANTUM Phytase (an E. coli derived phytase) 2500D for broiler is 500 FTU/kg feed. This dose is achieved at an inclusion rate of 200 grams of 2500D per metric ton of feed, which corresponds to a 5000-fold dilution of the product in feed. Therefore, a highly sensitive assay is required for accurate measurement of phytase activity in feed. For maximum assay sensitivity it is critical that the conditions of the assay are set at the optimal pH and temperature for the enzyme. As mentioned above, the assay conditions for phytase activity measurement described in the AQAC method (Engelen, A. J., et al. 2001) and which define the standard phytase unit or FTU are optimal for Aspergillus niger phytase. However, these conditions are not optimal for phytases derived from other sources, such as E. coli, and when used compromise assay sensitivity and reliability.

Improving the signal-to-noise ratio for phytase activity measurements increases assay accuracy but does not however reduce the observed large variation in assay results across both replicate feed batch samples and across replicate sub-samples of batch samples. Factors contributing to assay variability across samples and sub-samples were mentioned above and include heterogeneous distribution of the phytase enzyme in the sample and inefficient or non-quantitative extraction of the enzyme, especially from steam conditioned and pelleted feed. These observations demonstrate the need for consistent sample processing as well as an efficient procedure for extracting phytase activity from animal feed samples.

Therefore, there was an unmet need for a reproducible and reliable measurement of enzyme activity in feed samples when the enzyme is added pre-pelleting or added as a granule. The present invention has significant improvements to the traditional in-feed enzyme assay making it possible to obtain reproducible, reliable measurements of enzyme activity in replicate samples taken from animal feed batches. The improvements of the present invention are using a larger feed batch sample size, grinding the feed batch sample to a smaller particle size, and using an alkaline pH extraction buffer.

SUMMARY OF THE INVENTION

The invention relates to a method for extracting and measuring enzyme activity in feed, comprising the steps of:

a) grinding a feed sample of at least about 300 grams±30 grams so that about 80% of the material has a particle size of 250 μm or less to make a ground feed sample;

b) mixing the ground feed sample with an aqueous borate buffer of about 25 mM sodium borate at about pH 10.0;

c) extracting the enzyme from the ground feed sample; and d) measuring the enzyme activity under conditions that achieve optimal signal-to-noise ratio for the enzyme of interest.

BRIEF DESCRIPTION OF THE FIGURES

FIG. 6A is a graph showing the total phytase activity extracted from replicate flour samples. The phytase activity extracted from sample number 3 was defined as 100% (maximum phytase activity extracted).

FIG. 11A: Rep 1.

FIG. 12A (top) shows the average variability of the phytase activity measurement across replicate extractions. This variability is defined here as the inter-assay coefficient of varia-

DETAILED DESCRIPTION OF THE INVENTION

Figure 1:
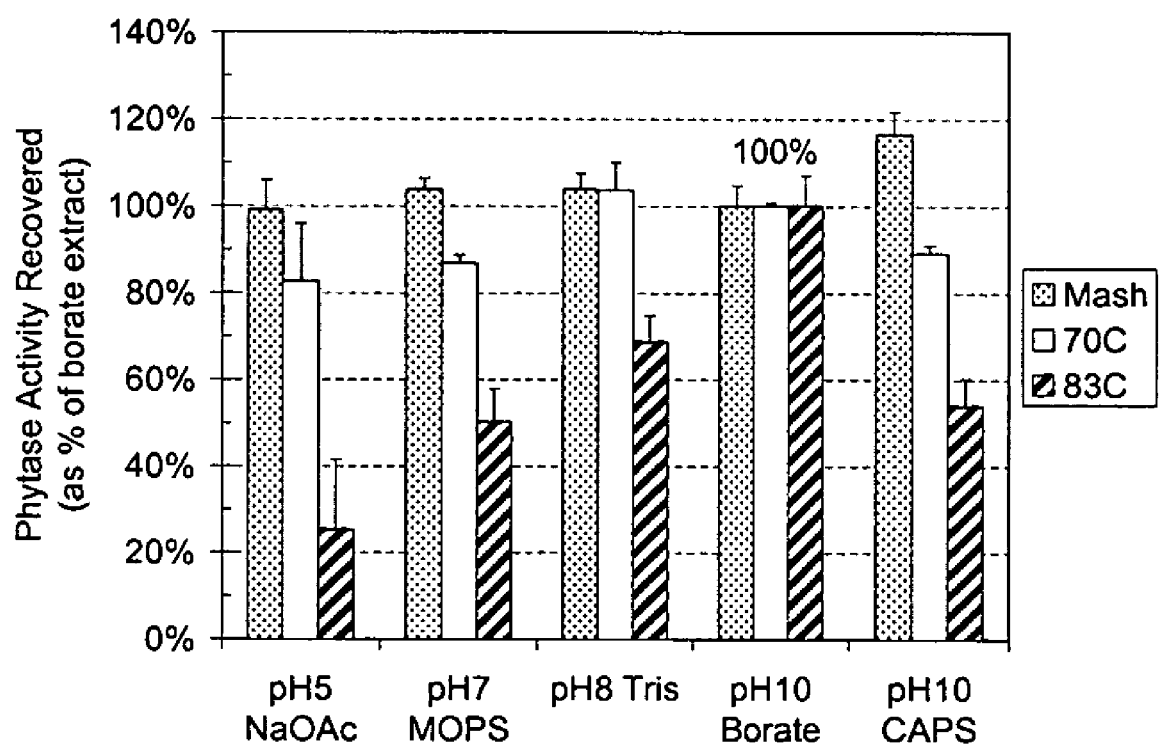
FIG. 1 is a graph showing that sodium borate buffer at pH 10 recovers more phytase activity from pelleted feed compared to other buffers at pH 5, 7, 8, and 10. 70° C. and 83° C. refer to the feed conditioning and pelleting temperatures. Buffer concentrations were all 25 mM TWEEN 20 was not added. Relative phytase activities in the plot were expressed as the percent of the enzyme activity recovered using borate (pH 10) buffer.

The invention relates to a method for extracting and measuring enzyme activity in feed, comprising the steps of:

a) grinding a feed sample of at least about 300 grams±30 grams so that about 80% of the material has a particle size of 250 μm or less to make a ground feed sample;

b) mixing the ground feed sample with an aqueous borate buffer of about 25 mM sodium borate at about pH 10.0;

c) extracting the enzyme from the ground feed sample; and d) measuring the enzyme activity.

The method further relates to when the enzyme is a phytase, amylase or cellulase. A further embodiment is wherein the phytase is an *E. coli* phytase or a phytase derived from *E. coli*. Another embodiment is where the phytase is Quantum™ Phytase.

The invention also relates to where the feed sample is a mash or pelleted feed sample.

The invention also relates to when measuring the enzyme activity is a phytase assay performed at pH 4.5 and 60° C.

The invention relates to measurement of enzyme activity, wherein the feed enzyme was produced in a transgenic plant. In particular, wherein the feed enzyme is phytase, cellulase or amylase.

The invention will be further described by reference to the following detailed examples. These examples are provided for purposes of illustration only, and are not intended to be limiting unless otherwise specified.

EXAMPLES

Example 1

Handling and Milling Feed Samples Containing QUANTUM Phytase

This method describes the processing and milling of animal feed samples containing QUANTUM Phytase 2500D in preparation for extraction of phytase activity for the enzyme assay.

| Equipment | |
|---|---|
| Hammer Mill | Perten Laboratory Mill 3100 or equivalent |
| Hammer Mill brush | Perten catalog #31.14.40 |
| Brush for cleaning cyclone | Perten catalog #31.04.30 |
| Plastic funnel | Perten catalog #31.02.60 |
| 0.8 mm screen | Perten catalog #31.02.30 |
| Plastic Baton | Perten catalog #31.04.30 |
| Dust Collection System | Unimaster 250-K7 similar, with 4-inch extraction arm |
| Explosion proof vacuum | Atrix International, Model #HCTV (recommended) |

| Consumables | |
|---|---|
| Plastic ZIPLOC | Fisher catalog #01-816E type bags |
| Dust masks | Any NIOSH approved N95, N99 or N100 respirator Fisher # 19-041-429 (recommended) |

Personal Protective Equipment

Use the following laboratory safety precautions when performing this method. Use Nitrile or Powder-free Latex gloves, lab coat, safety glasses, dust mask, and hearing protection. Keep hands, clothing and hair clear of the grinding mill. Unplug mills before cleaning and when removing and replacing parts and receptacles. Do NOT stir grain in hoppers with hands. Clean up work area with vacuum when finished. Empty vacuum after each use to prevent accumulation of flour and mold infestation.

Mixing. If primary sample size exceeds 330 g, the following mixing procedure is required. Primary sample bags should be rotated a minimum of 12 times in each direction (12 times end over end, 12 times to the left, etc.) before the bag is opened and the secondary sample collected. If there is not enough room to mix the primary sample in the bag, empty the contents into a container with an equal sample volume of empty space before mixing.

Milling. Place the plastic funnel directly on the mill so feed flows directly into the mill chamber. Do not use the vacuum feed control accessory which is normally positioned between the funnel and mill, as this will quickly plug up with feed. Caution: do not put fingers in funnel while operating mill.

Grind 300 g of well mixed* feed in a Perten 3100 Hammer Mill using a screen with 0.8 mm pore size. Slowly (at the rate of 100 g of feed per minute or slower) add feed into the mill in order to prevent heating of the feed and/or clogging the screen. *Note that if the primary sample size is greater than 330 g, the primary sample should be mixed thoroughly as described above under "Mixing" before the 300 g secondary sample is removed prior to grinding in the Hammer Mill. If the primary sample size is ≧100 grams but ≦330 grams mill the entire primary sample and record the umixed/unmilled sample weight in the submitted report.

When milling a series of samples measure and record the temperature of the first sample milled immediately after transfer to the storage bag. For all subsequent samples do not allow the post-milling temperature to increase more than 5° C. above the temperature of the first milled sample. Otherwise allow additional time for the mill to cool after cleaning before continuing with the next sample.

Clean the mill between each sample using Perten Hammer Mill brush, Plastic baton and vacuum. Mix the milled sample well before storage and again before removing milled sub-samples for analysis. It is recommended (Appendix 1) that the primary samples submitted are 300 g (±30 g) and that all 300 g of the primary sample is hammer milled. If replicates are included, they need to be labeled clearly with a unique identifier. Each of the 300 g feed samples should be ground separately and assayed separately. Samples should be ground in order from lowest to highest dosage (with cleaning between each sample).

Example 2

Preparation, Storage and Handling of Control and Check Samples for Quantum Phytase In-Feed Assay Principle. This method describes preparation of QUANTUM "25D" QUANTUM 2500D diluted 100-fold). 25D is used for controls II and III in QUANTUM ™Phytase In-Feed analytical method described in Example 3 below. Also, this method describes the storage and handling of feed check samples containing QUANTUM Phytase 2500D.

Materials
QUANTUM "25D" Standard
QUANTUM 2500D
Wheat carrier
Milled feed check samples
Zip-loc™ plastic bags, 50-ml plastic centrifuge tubes, Falcon™ type and Humidity sponges with color indicator.

Sample milling and mill cleaning: Follow 'Handling and milling feed samples containing Quantum™ Phytase 2500D" in Example 1, supra.

Preparation of QUANTUM 25D control: Mill 320 g of dry wheat carrier. Clean mill. Mill 10.0 g of QUANTUM Phytase Dry product (QUANTUM 2500D). Weigh 297.00 g of milled dry wheat carrier and place into plastic bag. Weigh 3.00 g of milled QUANTUM sample and combine with sample of wheat carrier. Seal the bag and mix "25D" thoroughly as described in Example 1.

After mixing, open bag and exclude air from the bag. Place this bag into another plastic bag. Add two or more humidity sponges, exclude air and seal outer bag. Monitor at regular intervals and replace humidity sponges as needed. Store bag containing 25D at 4° C. Alternatively store the samples in the cold (preferably 4° C.) and at low relative humidity (preferably <30% RH).

Storage of feed check sample: Place milled feed sample in a plastic bag. Exclude air from the bag. Place this bag into a second plastic bag. Add at least 2 humidity sponges in the second bag. Exclude air from the outer bag and seal. Do not seal inner bag containing feed. Monitor at regular intervals and replace humidity sponges as needed. Store at 4° C. The feed must be kept cold (to prevent infestation by insects) and dry (to prevent molding). IMPORTANT: Do not seal the inner bag so that the humidity sponge can absorb the humidity of the inner bag as well. Alternatively store the samples in the cold (preferably 4° C.) and at low relative humidity (preferably <30% RH).

Weighing milled feed samples for extraction: Before weighing sub-samples equilibrate double-bagged milled feed to room temperature for at least 2 hours. Weigh 4.5000 g (±0.050 g) of the sample, record the weight and sample name onto the side of the tube. Place sample in labeled tube and seal with cap.

Example 3

Determination of Extractable Phytase Enzymatic Activity from Feed at pH 4.5 and 60° C. by Inorganic Phosphate Release This procedure includes a method for extracting phytase enzyme from feed, followed by enzymatic assay of the extracted phytase. The phytase assay is based on the detection of inorganic phosphate released from sodium phytate substrate by the hydrolytic action of phytase enzyme. The enzymatic reaction is carried out for 60 minutes at pH 4.5 and 60° C., followed by simultaneous quenching of the reaction and color development. Color development, which is measured spectrophotometrically at 415 nm, is the result of complex formation of enzymatically released inorganic phosphate with molybdate and vanadate ions of the coloring-reagent.

One QUANTUM Phytase unit (QPU) is the quantity of enzyme that liberates 1 µmol of inorganic phosphate, from sodium phytate per minute at 60° C. and pH 4.5. The QUANTUM Phytase unit (QPU), defined here, is DIFFERENT from the international phytase unit (FTU); the conversion factor (QPU/FTU) being approximately equal to 5.66 for QUANTUM Phytase. (The conversion factor can be determined empirically for each set of analyses by comparing the assay result for Control 25D described in Example 2 and the phytase activity of the original batch in FTU/g.) FTU is defined as the quantity of enzyme that liberates 1 µmol of inorganic phosphate, from sodium phytate, per minute at 37° C. and pH 5.5. Note that phytase enzyme activities in feed samples and QUANTUM Phytase samples (dry and liquid) are often labeled in FTU.

| Chemicals | |
|---|---|
| Acetic acid, glacial, 17.55 mol/L ($CH_3COOH$) | Fisher #A38-500 or equivalent |
| Ammonium hydroxide solution, 29% w/v ($NH_4OH$) | Fisher # A669-500 or equivalent |
| Ammonium metavanadate ($NH_4VO_3$) | Sigma # A-1183 or equivalent |
| Ammonium molybdate tetrahydrate, $(NH_4)_6Mo_7O_{24}4H_2O)$ | Fluka # 09880 or equivalent |
| Nitric Acid, concentrated >65% ($HNO_3$) | Fisher #A200-500 or equivalent |
| Phytic Acid (dodecasodium salt from rice, ($C_6H_6O_{24}P_6Na_{12}$) | Sigma # P-3168 (no substitution) |
| Sodium acetate trihydrate ($CH_3COONa.3H_2O$) | Fisher # BP334-1 or equivalent |
| Sodium borate decahydrate ($Na_2B_4O_7,10H_2O$) | Sigma # S-9640 or equivalent |
| Sodium Hydroxide (NaOH) | Sigma # S-0899 |
| TWEEN (polyoxyethelene sorbitan monolaurate | Sigma # P-7949 or equivalent |

| Equipment (equivalents may be substituted) | |
|---|---|
| Analytical Balance | Mettler Toledo AB54-S or equivalent |
| Centrifuge | Eppendorf 5810R or equivalent |
| Lab Timer | |
| pH Meter | Mettler Toledo MP220 with a high quality electrode pH Standards pH 7.0 and 4.0 solutions |
| Pipettors | Gilson PIPETMAN P-200, P-1000, P-5000 |
| Repeat pipettors | Eppendorf Repeater Plus |
| Rugged Rotator | Glascol 099A 0616700026 (base unit) with RD50 test tube rack head |
| Volumetric Flasks | 50 mL wide-neck, 100 mL, 250 mL, and 1.0 L |
| Vortex Mixer | Fisher VORTEX GENIE 2 or equivalent |
| Waterbath | Fisher Scientific Isotemp 228 or equivalent set at 60 +/− 0.5° C. |
| Spectrophotometer | Spectromax Plus$^{385}$ Molecular Devices or equivalent |

| Consumables | |
|---|---|
| Centrifuge Tubes 50 mL | Fisherbrand 06-443-20 or equivalent |
| Cuvettes | Fisherbrand 14-385-942 disposable plastic or equivalent |
| Test Tubes 15 mL | Fisherbrand 14-961-29 or equivalent |

General Comments. Follow all appropriate laboratory safety precautions when performing this assay. Ensure that reagents and glass wares are free of phosphate contamination. Pipettors and analytical balances must be calibrated regularly. Use deionized water to prepare all reagents and test solutions. Following the assay collect all samples containing color stop solution in a separate waste container and dispose accordingly. All centrifugations should take place in a centrifuge with its temperature dial set at room temperature.

Preparation of Reagents

Ammonium Heptamolybdate Stock Solution. Dissolve 100 grams of ammonium heptamolybdate in 900 mL of deionized water. Add 10 mL of ammonium hydroxide (29%) and quantitatively transfer to a 1.0 L volumetric flask. Adjust the volume to 1.0 L with deionized water and wrap the flask with aluminum foil to shield from light. Keep at room temperature protected from light for up to 30 days.

Ammonium Vanadate Stock Solution. Dissolve 2.35 grams of ammonium vanadate in 800 mL of deionized water in a volumetric flask. Cover the mouth of volumetric flask tightly with several layers of PARAFILM. Heat the sample in a 60° C. water bath to aid dissolution. Once the ammonium vanadate has completely dissolved, under a well-ventilated fumehood, slowly add 20 mL of diluted nitric acid while stirring. (Diluted nitric acid is made by adding 7 mL of concentrated nitric acid to 13 mL of deionized water.) Cool to room temperature, transfer to a 1.0 L volumetric flask and adjust the volume to 1.0 L with deionized water. Wrap the flask with aluminum foil to shield from light. Keep at room temperature protected from light for up to 30 days.

Color Stop Solution. The amount of color stop solution that will need to be made will vary depending on the number of samples that are to be analyzed. Preparation of this solution should be carried out under a well-ventilated hood. For 100 mL of color stop solution mix 25 mL of ammonium heptamolybdate stock solution with 25 mL of ammonium vanadate stock solution. To this mixture slowly add 16.5 ml of diluted nitric acid (7 mL of concentrated nitric acid and 13 mL of deionized water) with constant mixing to avoid precipitation. Adjust the volume to 100 mL with deionized water in a volumetric flask. The color of the stop solution should be faint yellow. Following the assay collect all samples containing color stop solution in a separate waste container and dispose accordingly. Prepare fresh on calendar day of use.

Acetate Buffer, 250 mM, pH 4.5. Dissolve 12.04 grams of sodium acetate trihydrate in 900 mL of deionized water along with 9.2 mL of glacial acetic acid. Adjust the pH of the sample to 4.5 using either acetic acid or diluted sodium hydroxide. To this add 1.0 mL of a 10% Tween™ 20 solution (w/v). Quantitatively transfer the material to a volumetric flask and adjust the volume to 1.0 L with deionized water. Keep at 4° C. for up to 30 days.

Sodium Phytate Substrate (9.09 mM). Dissolve 2.1 grams (2.27 mmoles) of sodium phytate in approximately 200 mL of 250 mM acetate buffer pH 4.5. Adjust the pH, at room temperature, to 4.5 using acetic acid. Transfer the solution to a 250 mL volumetric flask and adjust the volume to 250 mL with acetate buffer pH 4.5. Prepare fresh on calendar day of use.

Potassium Phosphate Standard (7.2 mM). Weigh out 0.980 grams of potassium dihydrogen phosphate and dissolve in 250 mM acetate buffer in a 1.0 L volumetric flask. Adjust the pH to 4.5, if necessary with acetic acid or sodium hydroxide the pH, and adjust the volume to 1.0 L with 250 mM acetate buffer pH 4.5 (5.4). Keep at 4° C. for up to 90 days.

TWEEN 20 Solution (10% w/v). Dissolve 5 grams of TWEEN 20 in 40 mL of deionized water in a volumetric flask and adjust the volume to 50 mL with deionized water. Keep at 4° C. for up to 3 months.

Sodium Borate Extraction Buffer, 25 mM, pH 10.0. Dissolve 9.53 grams of sodium borate in 900 mL of deionized water. Adjust the pH of the buffer to 10.0 using diluted sodium hydroxide. If designated, one may add to this add 1.0 mL of a 10% Tween™ 20 solution. Transfer the material to a 1.0 L volumetric flask and adjust the volume to 1.0 L with deionized water. Keep at 4° C. for up to 30 days.

Sample Preparation and Phytase Enzyme Assay (a) Milling. Milling was performed as described in Example 1 above which describes handling and milling feed samples containing Quantum™ Phytase 2500D.

(b) Control & Check Sample. Include a control and a check sample with each assay.

I. Control 25D: For a QUANTUM dry standard add 90 mg QUANTUM 25D to a 50 mL centrifuge tube followed by 42 mL of borate extraction buffer. This quantity of 25D suspended in 42 ml buffer corresponds to a 4.5 gram feed sample containing QUANTUM 2500D at an inclusion rate of 200 grams per tonne. At this inclusion rate QUANTUM Phytase 2500D will deliver a final dose of 500 FTU/kg of feed.

II. Check sample: a mash feed sample with known amount of extractable phytase activity. Samples of 25D and feed check samples can be obtained from Syngenta Animal Nutrition (3054 Cornwallis Rd., Research Triangle Park, N.C. 27709, USA). Perform at least duplicate extractions for the control 25D and the check sample. Assay each extract in triplicate.

(c) Phytase Extraction. For each 300 g milled sample, prepare three 50 mL centrifuge tubes each containing 4.50 g+/−0.050 g of finely ground feed. (Prior to weighing out the sample, mix the ground feed well.) Place the tube on the balance. Tare the balance and add 42 mL of sodium borate extraction buffer to the tube. The extraction buffer should be at room temperature before use. Record the mass of the added buffer. Close cap tightly, shake until all of feed is suspended and mix on rotator for 30 minutes at room temperature (~22° C.). Select a rate of stirring that keeps all the feed suspended throughout the extraction procedure (70-75 on the "Rugged" rotator). Centrifuge the solution for 10 minutes at 1800×g. The supernatant fraction will be used as the enzyme stock. The supernatant may have two layers, a relatively clear bottom layer and the upper cloudy layer. It is this bottom layer that should be used for the assay. Dilute the supernatant from each extraction as described in section (d). Then, use diluted supernatant (from each extraction) for triplicate assays. The supernatant should be stored at 4° C. Begin the assay reaction within three hours of the extraction.

(d) Assay Working Dilution. On a tared balance add and record the mass of 0.5 mL of extracted enzyme from section (c). Add 4.5 mL of acetate buffer using repeater pipette and record the total mass of the extract and buffer. Vortex dilutions and centrifuge at 1800×g for 10 minutes to remove precipitated salts (5 mL sample volume recommended). With this 1:10 dilution, mash feed containing QUANTUM phytase at 500 FTU/kg is expected to observe an $OD_{415}$ between 0.9 and 1.1 in the Endpoint Assay.

Determining optimal dilution: When the expected level of phytase activity is not know, a rapid range finder study may be required to determine the optimal dilution rate to get a particular sample analysis onto scale. The range finder study is conducted by preparing the extraction as below. Variations to the assay are then made with regards to the preparation of the working dilution listed below.

For the range finder study a set of working dilutions is made on a volumetric basis, and these are then run through a modified Quantum™ phytase assay. The range finder assay may be run with only a single reaction tube for each dilution to be tested and with no reaction blanks. Once the optimal dilution rate has been determined, continue the assay by preparing working dilutions according to the protocol detailed below. The target absorbance at 415 nm is between 0.4 and 1.1. The standard curve has been observed to remain linear into the range of OD 1.4. Calculation of the working dilution: Take the mass of the extraction and divide that value by the total mass of liquid in the test tube. The inverse of that number will be the working dilution factor.

Phosphate Standard Curve. Use the standard potassium phosphate prepared as above and the acetate buffer above to make up the following phosphate standards:

TABLE 1

Phosphate Standard Curve

| Standard | Vol of acetate buffer (μL) | Vol of 7.2 mM Phosphate (μL) | Phosphate (μmols) |
| --- | --- | --- | --- |
| 1 | 500.0 | 0.0 | 0.000 |
| 2 | 450.0 | 50.0 | 0.360 |
| 3 | 425.0 | 75.0 | 0.540 |
| 4 | 400.0 | 100.0 | 0.720 |
| 5 | 375.0 | 125.0 | 0.900 |
| 6 | 350.0 | 150.0 | 1.080 |
| 7 | 300.0 | 200.0 | 1.440 |

Aliquot the phosphate/buffer volumes listed in the table above into test tubes. Add 1.0 mL of sodium phytate substrate to each standard tube and vortex to mix. Add 1.0 mL of color stop solution to the standards following the assay, and mix. Allow 5 minutes at room temperature for completion of the color reaction; this is followed by centrifugation at 1800×g for 10 minutes clarify the solution prior to absorbance measurements. Spectroscopic measurements should be taken within 90 minutes after reaction quenching. A phosphate standard curve must be prepared each time a set of assays is performed. Absorbance for the test enzyme samples should be within the absorbance range of the standard curve. If not, dilute the samples further and repeat the assay.

Phytase Enzyme Assay

Aliquot 1.0 mL of sodium phytate substrate into 15 mL test tubes and pre-incubate for 2 minutes at 60° C. (see summary of sample/reagent additions below). Prepare three test tubes for the enzyme reactions and three for the reaction blanks for each enzyme sample (6 substrate tubes total per sample). Pre-incubate the 5 mL working dilution enzyme samples prepared as described above for 2 minutes at 60° C.

Following the 2 minutes of pre-incubation, add 0.5 mL of working dilution test sample to 3 of the 6 substrate tubes. Start a timer upon the addition of diluted enzyme to the first tube. Continue adding diluted enzyme sample to the second and third sodium phytate substrate tubes at a constant rate (i.e. addition of diluted enzyme to a tube every 5 seconds; but do not add diluted enzyme to the three blank tubes at this stage in the assay. The constant enzyme addition rate established during this portion of the assay will be required again during the reaction quenching protocol. After addition of the last aliquot of diluted enzyme, vortex all reaction tubes and quickly return them to the 60° C. water bath. Incubate for 60 minutes. Incubate working dilution of enzyme side by side with the reactions (in the 60° C. water bath for the 60 minute reaction time) to minimize difference between sample and corresponding blank.

Following the 60 minute incubation period, add 1.0 mL of color stop solution to each enzyme reaction test tube and also to each blank test tube using the constant sample addition rate established above (use of repeat-pipettor may increase the efficiency of the process). Vortex all quenched test tubes.

After the blank reaction tubes have been quenched with color stop solution add 0.5 mL of enzyme working dilution to each.

Subsequent to the addition of color stop reagent to all test tubes vortex samples again to ensure complete mixing of reagents, allow 5 minutes for completion of the color development and centrifuge at 1800×g for 10 minutes to clarify samples prior to taking absorbance measurements. Spectroscopic measurements should take place within 90 minutes of quenching.

Spectroscopic Measurements and Activity Calculations

Using either a plastic (1 cm path length, semi-micro), glass or quartz cuvette, read all reaction, blank, and phosphate standard curve samples at 415 nm and record values. Take care not to disturb the precipitated material in the test tubes when transferring the solution to cuvettes following centrifugation.

Each extraction will have 6 cuvettes associated with it. The contents of each assay tube will be poured into a different cuvette. Read the three reactions before reading the three background cuvettes. This order is necessary for proper calculation of activity in the calculation spreadsheet.

Calculate a corrected absorbance for each phosphate standard curve sample by subtracting the 0 μmol phosphate absorbance measurement. The standard curve is generated by plotting the absorbance at 415 nm as a function of μmols of phosphate. The standard curve is displayed along with the linear regression parameters.

The μmols of phosphate detected in the assay is calculated by using the background corrected absorbance for each replicate and interpolating it using the phosphate standard curve regression parameters.

QPU is defined as μmols/min at pH 4.5 and 60° C. Units/mL is calculated by dividing μmols of phosphate by the 60 minute reaction time and then by the volume of diluted enzyme added to the reaction (0.5 mL).

QPU/mL in the extraction buffer is then calculated by multiplying the QPU/mL in the diluted extract by the dilution factor.

To determine the units of enzyme in the feed, the QPU/mL in the extract is multiplied by the mass of the extraction buffer and divided by the weight of the feed extracted.

A worksheet can be used to average the absorbance readings from the triplicate assays and the triplicate background readings along with a standard deviation and % co variation for each extract. Ideally, the three readings should have a CV of less than 6% and fall into the absorbance range of 0.4 to 1.1.

The above protocol was performed as described above to measure phytase in samples sent to five labs. The data are shown in Tables 2 and 3.

Extractions were performed on mash and pelleted feed samples that contained Quantum™ Phytase added pre-pelleting as a dry formulation.

TABLE 2

Phytase activity recovered from mash and pellet feed samples manufactured at 4 mills (A, B, D, E) and analyzed at 5 labs (1–5). Labs 1, 2, 4, and 5 used analytical method described in Example 3 and lab 3 used the high throughput method of Example 4. Product 25D is the Control 25D samples described in Example 3. This product has a minimum guaranteed phytase concentration of 2500 FTU/g when used before the expiration date.

| Mill Code | Sample Type | Pellet temp. | Lab: 1 SOP 1.4 AVE | SD | Lab: 4 SOP 1.4 AVE | SD | Lab: 5 SOP 1.40 AVE | SD | Lab: 2 SOP 1.40 AVE | SD | Lab: 3 SOP 2.2 AVE | SD |
|---|---|---|---|---|---|---|---|---|---|---|---|---|
| E | mash | mash | 4.30 | 0.56 | 3.49 | 0.08 | 3.60 | 0.91 | 2.94 | 0.28 | 4.15 | |
| E | pellet | 86.4 C. | 2.35 | 0.13 | 1.94 | 0.47 | 1.75 | 0.04 | 1.78 | 0.15 | 1.74 | |
| A | mash | mash | 3.07 | 0.15 | 3.07 | 0.33 | 2.95 | 0.05 | 2.96 | 0.52 | 2.88 | |
| A | pellet | 82 C. | 1.06 | 0.08 | 0.87 | 0.04 | 0.87 | 0.10 | 0.65 | 0.06 | 1.08 | |
| D | mash | mash | 3.40 | 0.59 | 3.28 | 0.33 | 3.08 | 0.15 | 2.81 | 0.21 | 3.71 | |
| D | pellet | 85 C. | 0.85 | 0.14 | 0.50 | 0.02 | 1.15 | 0.01 | 0.54 | 0.08 | 0.84 | |
| B | mash | mash | 3.48 | 0.11 | 3.20 | 0.15 | 3.35 | 0.28 | 2.72 | 0.09 | 3.54 | |
| B | pellet | 85 C. | 3.25 | 0.37 | 2.46 | 0.16 | 2.72 | 0.22 | 2.61 | 0.13 | 3.17 | |
| | product 25D | | 3.79 | 0.16 | 3.44 | 0.20 | 3.75 | 0.16 | 3.39 | 0.09 | 3.15 | |

TABLE 3

Average phytase activity recovered from 8 feed samples as measured by 5 labs using 2 method formats (Examples 3 and 4). These are the lab-to-lab averages of the data reported in Table 2.

| Mill Code | Sample Type | Pellet temp. | Actual Dosage[b] FTU/Kg | Expected QPU/g[a] | AVE (QPU/g) | SD (QPU/g) | CV | % of expected |
|---|---|---|---|---|---|---|---|---|
| E | mash | mash | 500 | 2.83 | 3.70 | 0.55 | 14.8% | 131% |
| E | pellet | 86.4 C. | 500 | 2.83 | 1.91 | 0.26 | 13.4% | 68% |
| A | mash | mash | 500 | 2.83 | 2.98 | 0.08 | 2.7% | 105% |
| A | pellet | 82 C. | 500 | 2.83 | 0.90 | 0.17 | 19.0% | 32% |
| D | mash | mash | 500 | 2.83 | 3.25 | 0.34 | 10.4% | 115% |
| D | pellet | 85 C. | 500 | 2.83 | 0.78 | 0.27 | 34.2% | 27% |
| B | mash | mash | 500 | 2.83 | 3.26 | 0.33 | 10.1% | 115% |
| B | pellet | 85 C. | 500 | 2.83 | 2.84 | 0.35 | 12.3% | 100% |
| | product 25D | | 500 | 2.83 | 3.50 | 0.27 | 7.6% | 124% |

Example 4

High Throughput Version of Determination of Extractable Phytase Enzymatic Activity from Feed at pH 4.5 and 60° C. by Inorganic Phosphate Release This version of the phytase assay introduced a new format for higher throughput and convenience. It replaces for example the glass flasks used for extractions with plastic Falcon tubes, and replaced dilutions and assays with glass culture tubes with plastic 96-well blocks and plates.

This extraction method and assay are developed for the determination of QUANTUM Phytase activity in animal feed samples. This method measures QUANTUM Phytase activity in feed that is targeted to have approximately 500 FTU/kg of enzyme activity. This assay is based on the detection of inorganic phosphate released from sodium phytate substrate by the hydrolytic enzymatic action of phytase.

Phytase (Myo-Inositol hexakisphosphate phosphohydrolase) is an enzyme that catalyzes the release of phosphate from phytate. Activity of phytase in feed is determined by extracting phytase from feed samples using borate buffer (pH 10.0) and subsequent diluting of the extract to an appropriate concentration. A portion of these diluted extracts are then incubated with sodium phytate for 60 minutes at 60° C., pH 4.5, followed by simultaneous quenching and calorimetric detection. The inorganic phosphate generated complexes with molybdate and vanadate ions resulting in color formation. The absorbance of the yellow-colored vanadomolybdophosphoric acid, whose concentration is proportional to the phosphate ion concentration in the reaction mixture, is measured at a wavelength of 415 nm. The measured absorbance is used to determine the phosphate ion concentration by comparison to a phosphate standard calibration curve.

Assay interferences may be caused by contaminates in solvent, reagents, glassware, and other sample processing apparatus. Ensure that reagents and glassware do not get contaminated with phosphate. All reagents and apparatus must be routinely demonstrated to be free from interferences under the conditions of the assay by running a matrix blank sample with each assay. Use high purity reagents and solvents to minimize interference problem. Other interferences may be caused by contaminates that are co-extracted from the sample matrix. The extent of matrix interferences will vary from source to source, depending upon the nature and diversity of the manufacturing complex or sampling procedures. Some samples may have other background material that also absorb at 415 nm and therefore interfere with determination of enzyme activity. This assay is only for activity determination of phytase in feed at described conditions.

Apparatus (equivalents may be substituted)
UV/VIS spectrophotometer, SPECTRA MAX PLUS 384, Molecular Device
Data collection system, SOFTMAX Pro Std.
VORTEX GENIE , Fisher brand, Cat. # 12-812.
Analytical Balance with 0.1 mg resolution, Mettler XS204 balance
Centrifuge, Eppendorf 5810R
Rugged Rotators Glascol 099A 0616700026 (base unit) with RD50 test tube rack head
Lab Timer, various Fisher brand
pH Meter, Mettler Toledo MP220 with a high quality electrode
pH Standards, pH 10, 7.0 and 4.0 solutions
Pipettors, Gilson PIPETMAN P-200, P-1000, P-5000
Circulator temperature control Water bath, Fisher Scientific
Various glassware and consumables
Magnetic stirrers with stirring bars and or orbital shaker/or rotator for mixing of samples
Eppendorf Repeater Pipettors, Repeater plus pipette (Cat # 21-380-9), and Cat # 21-381-115, for 25 mL repeater
Single and multi-channel pipettes
Centrifuge Tubes 50 mL, Fisher brand 06-443-20 or equivalent
96 well-well plates, COSTAR Assay/Path Flat bottom clear Plates, COSTAR
12-deep-well blocks, VWR 12-Channel Reservoir Cat. #82007-294
96-deep-well blocks, Greiner Master Block 1.2 mL. ISC-Bioexpress Cat. #T-3058-4
Reagents and Supplies (equivalents may be substituted)
Certified Dry QUANTUM Phytase, Syngenta Animal Nutrition
Wheat based feed Matrix, Syngenta Animal Nutrition
Corn-soy based Feed matrix, NCSU (North Carolina State University)
Acetic acid (glacial), Fisher #A38-500 or equivalent
Ammonium hydroxide solution (29% w/v), Fisher # A669-500
Ammonium metavanadate, Sigma # A-1183
Ammonium molybdate tetrahydrate, Fluka # 09880
Nitric Acid (concentrated>65%), Fisher A200-500
Phytic Acid (dodecasodium salt from rice), Sigma, Lot # 094K 1094, P-3168
Potassium dihydrogen phosphate, Fisher # BP362-1 or equivalent
Sodium acetate trihydrate, Fisher # BP334
TWEEN 20 (polyoxyethelene sorbitol monolaurate), Sigma Lot # 011560, BP 337-500
Borate decahydrate ($Na_2B_4O_7$, $10H_2O$), Sigma # P-7949
Sodium Hydroxide (NaOH)

Prepare and label three 50 mL centrifuge tubes for each sample. Make sure all feed samples are at room temperature prior to weighing out. Tare a certified analytical balance to zero and then record the weight of each empty 50 mL centrifuge tube and tube cap. To each 50 ml tube add 4.50 g of milled feed. Record the exact weight (mass in grams of sample used in each extraction). Obtain one 0.3 FTU/g, two 0.5 FTU/g, and one 0.8 FTU/g pre-weighed standards.

Using a calibrated analytical fluid dispenser add 42 mL of sodium borate buffer to each tube containing the measured feed. After adding sodium borate buffer to each sample, tare the balance and record the exact weight of the total tube weight. Calculate the buffer weight by subtracting both the tube weight and the feed weight from the total weight.

Close cap tightly then vortex and vigorously shake sample until all particulate matter is suspended.

Set timer and mix on the Rugged Rotator for 30 minutes at room temperature (~22° C.). The rotator's dial should be set at 70. Make sure that none of the samples are leaking and that the samples are being mixed.

Carefully remove samples from the rotator and then centrifuge samples for 10 minutes at 1800×g.

Carefully remove tubes from centrifuge and place into a tube rack. The supernatant may have two layers, a relatively clear layer directly under an upper cloudy layer. It is this clear layer that should be used for the assay working dilutions.

Assay Working Dilution

Using a calibrated P1000 pipettor, add 0.250 mL of extracted enzyme from the clear layer of the supernatant and dispense into a 12-deep-well block.

Using a calibrated autodispenser, add 4.75 mL of sodium acetate buffer to each well of the 12-well plate containing the extracted enzyme from step. This will result in a 1:20 working dilution. Mix dilutions well by rocking block back and forth. Make sure not to spill or cross contaminate any of the contents.

Centrifuge dilutions for 10 minutes at 1800×g to remove all precipitated salts.

Determining optimal dilution: If a working dilution other than 1:20 is required to get the assay on scale, adjust the ratio of extracted material with 250 mM sodium acetate buffer accordingly. Keep the final volume of each working dilution at 5 mL. A 1:20 dilution of mash feed containing Quantum™ Phytase at 500 (FTU/kg) is expected to have $OD_{415}$ reading between 0.4 and 0.8 in this Endpoint Assay.

Phytase Enzyme Assay

In a 96 deep-well block, assign three wells each for both the enzyme reactions and blank reactions. This should result in six wells for each sample.

To a clean 96 deep-well block, add 0.3 mL of sodium phytate substrate to the top six rows using a 12-well multichannel pipettor.

Place the 96 deep-well block containing substrate and the 12 well plates containing enzyme extract into a 60° C. water bath and allow contents to pre-incubate for 2 minutes.

Following the 2 minute pre-incubation, set timer for 60 minutes and immediately add 0.15 mL of working dilution from the 12-well block to the first three rows (A-C) of the 96 deep-well block. A 12-well multichannel pipettor may be used in this step. However be sure to add enzyme extract to the appropriate wells and change tips between dispensing each sample.

Quickly vortex samples in the 96 deep-well block and place block directly back in the 60° C. water bath. Make sure not to cross contaminate or spill contents by mixing with the vortex too vigorously.

During enzyme assay incubation, prepare phosphate standards. Make two separate sets of standards. Make sure not to add color stop solution at this time to standards.

Following the 60-minute incubation, add 0.3 mL of color stop solution to all enzyme reactions and blank reactions in the 96 deep well block using a 12-well multichannel pipettor.

Remove both the 96 deep-well block and the 12-well block from the 60° C. water bath. Vortex and mix contents in 96 deep well block thoroughly.

Add 0.15 mL of enzyme working dilution from the 12-well block to each of the blank reaction wells of the 96 deep-well block. All wells for each sample (rows A-F) should now contain a total of 0.75 mL of solution.

Vortex each 96 deep-well block to mix contents thoroughly. Allow 5 minutes for completion of the color development. At this time add 1 mL of color stop solution to the phosphate standards prepared earlier. Centrifuge each 96 deep-well block for 10 minutes at 1800×g. Centrifuge phosphate standards for 10 minutes at 1800×g. Carefully remove block(s) and tubes from centrifuge.

Spectroscopic Measurements and Activity Calculations

Use a 12-well multichannel pipette to transfer 0.3 mL of clear solution to a clean spectrophotometer readable 96 well plate. Make sure not to disturb the precipitated material in the wells following centrifugation. Also, use a pipette tip to pop any bubbles in the 96-well plate prior to reading on the spectrophotometer. Alternatively the 96 well-plate can be spun at 800×g for 1 minute to remove bubbles.

Add 0.3 mL of the phosphate standards to their appropriate wells.

Add 0.3 mL of sodium acetate buffer to any remaining empty wells. Use any spectrophotometer software or manual calculations can be carried out to obtain activity data using OD readings at 415 nm.

Place 96-well plate into tray of the spectrophotometer's plate reader and read the samples at the wavelength of 415 nm. Record readings.

Standard Phosphate Calibration Curve

Preparation of Potassium Phosphate Standard Stock Solution. Dry a sufficient amount of potassium dihydrogen phosphate in a vacuum oven at 100-104° C. for 2 hours. Cool to room temperature in desiccator. Prepare stock standard solution of potassium dihydrogen phosphate ($KH_2PO_4$), with concentration of 7.2 mM into a 1.0 L volumetric flask. Weigh out 7.2 mmoles (~0.980 grams depending on the purity of the product) of potassium dihydrogen phosphate and dissolve in approximately 800 mL of 250 mM sodium acetate buffer. Check the pH, and adjust as necessary to pH 4.5 with acetic acid or sodium hydroxide. Then, bring up to volume with sodium acetate buffer and mix thoroughly. Store this solution in a glass bottle at 4° C. for up to 30 days.

Preparation of Potassium Phosphate Standards. Use the standard potassium phosphate prepared as above and acetate buffer to make up the following phosphate standards:

TABLE 4

Phosphate Standard Curve

| Standard | Volume of acetate buffer μL | Volume of 7.2 mM phosphate μL | Concentration of phosphate in 2.5 ml final mixture μM |
|---|---|---|---|
| 1 | 500.0 | 0.0 | 0 |
| 2 | 450.0 | 50.0 | 144 |
| 3 | 425.0 | 75.0 | 216 |
| 4 | 400.0 | 100.0 | 288 |
| 5 | 375.0 | 125.0 | 360 |
| 6 | 350.0 | 150.0 | 432 |
| 7 | 300.0 | 200.0 | 576 |

Aliquot the phosphate/buffer volumes listed in the table above into test tubes. Add 1.0 mL of sodium phytate substrate to each standard tube and vortex.

Add 1.0 mL of color stop solution to the standards following the assay, and mix. Allow 5 minutes at room temperature for completion of the color reaction; this is followed by centrifugation at 1800×g for 10 minutes to clarify the solution prior to absorbance measurements. Spectroscopic measurements should be taken within 90 minutes after reaction quenching. A phosphate standard curve must be prepared each time a set of assays is performed.

Calculations: Plotting the Standard Phosphate Calibration Curve.

Plot the corrected absorbance at 415 nm ($\Delta OD_{415\,nm}$, the absorbance measurement of each phosphate standard calibration solution after subtracting the absorbance measured for the 0 μmol phosphate solution) as a function of phosphate concentration (in μM) on the X-axis. Next, using linear regression program generate the "best fit" line and its corresponding equation.

$Y = MX + B$ where,

Y = $\Delta OD_{415\,nm}$ (Y-axis of the plot)
M = slope of the standard phosphate calibration curve
X = μM of phosphate (X-axis of the plot)
B = intercept of the standard phosphate calibration curve Estimating the concentration of released inorganic phosphate due to phytase-catalyzed enzymatic reaction. Calculate μM concentration of phosphate ion concentration using the following equations:

$C = (H - B)/M$ where, C = concentration (μM) of Pi
$H = \Delta OD_{415nm} = OD_{415nm}$ for enzyme reaction sample — $OD_{415\,nm}$ for the enzyme background sample
B = intercept of the calibration standard curve
M = slope of the calibration standard curve.

Determining the Phytase Activity in a Feed Sample.

Determine phosphate activity in a sample using the equations provided below:

$A = [(C \times Vr/Va) \times (Vi/1000) \times Df]/(t \times Ws)$ where,
A = phytase activity expressed in μmoles of Pi released per minute per gm of feed sample
C = concentration of released Pi, expressed in μM; (C = (H−B)/M, as described above)
Vr = total volume (in ml) of the reaction mixture after addition of the color stop solution (0.75 ml as per the present assay)
Va = volume (in ml) of diluted enzyme extract used for each assay (as per the present assay it is 0.15 ml)
Vi = initial volume (in ml) (or mass, assuming density to be equal to 1) of extraction solution (as per the present SOP it is ~42 ml)
Df = working solution dilution factor [Df = Vd/Vt, where, Vd = volume (or mass, assuming density to be equal to 1) of extracted enzyme used for working dilution & Vt = final volume (or mass, assuming density to be equal to 1) of diluted enzyme extract]
t = time-period (in minute) of incubation during phytase assay (60 minute as per the present assay)
Ws = initial mass (in gm) of sample used for each extraction (~4.5 gm as per the assay)

The above high throughput phytase assay was performed with samples and had the results as above in Example 3 in Tables 3 and 4.

Example 5

Efficient Extraction of Phytase from both Mash and Pelleted Feed Using a Novel Borate Buffer is Required for Accuracy of Activity Assay Effect of Extraction Buffer pH on Recovery of Phytase Activity In order to optimize extraction of QUANTUM Phytase from pelleted feed we tested a variety of buffers and extraction conditions. In this experiment (FIG. 1) milled feed samples were extracted in five different buffers and at 4 pH conditions. The extraction efficiency of each buffer was tested on samples of mash feed and on samples of feed conditioned at 70° C. (70° C. pellets) and at 83° C. (83° C. pellets). The lower temperature of 70° C. is not typically used for conditioning feed, whereas the higher temperature of 83° C. is in the range used in the commercial manufacture of feed for poultry and swine. The results demonstrate that the efficiency of phytase extraction from conditioned and pelleted feed was dependent on both pH and on the chemical nature of the buffer.

The results of this experiment also show that the extraction efficiency of a particular buffer was highly dependent on the temperature of feed conditioning. In FIG. 1, the phytase activity extracted from milled feed samples using sodium borate pH 10 buffer was defined as 100% for each sample type (mash, 70° C. pellets, 83° C. pellets). For mash feed, buffers at pH 5, 7, and 8 extracted about 100% of the activity extracted by the sodium borate pH 10 buffer. CAPS buffer at pH 10 extracted about 117% of the activity extracted by sodium borate pH buffer. For 70° C. pellets, the other four buffers extracted at least 80% of the phytase activity compared to sodium borate pH 10 buffer. However, the sodium borate pH 10 buffer proved much more efficient than the other buffers at extracting phytase activity from feed conditioned at the higher temperature. The relative extraction efficiency of the sodium acetate pH 5 buffer on the 83° C. pellets was only about 25% compared to the sodium borate pH 10 buffer. MOPS pH 7 and CAPS pH 10 buffers extracted about half of the activity extracted by the borate pH 10 buffer. Finally, Tris pH 8 buffer was about 70% as efficient as the borate pH 10 buffer.

Effect of Extraction Buffer pH on Background Phosphate

Figure 2:
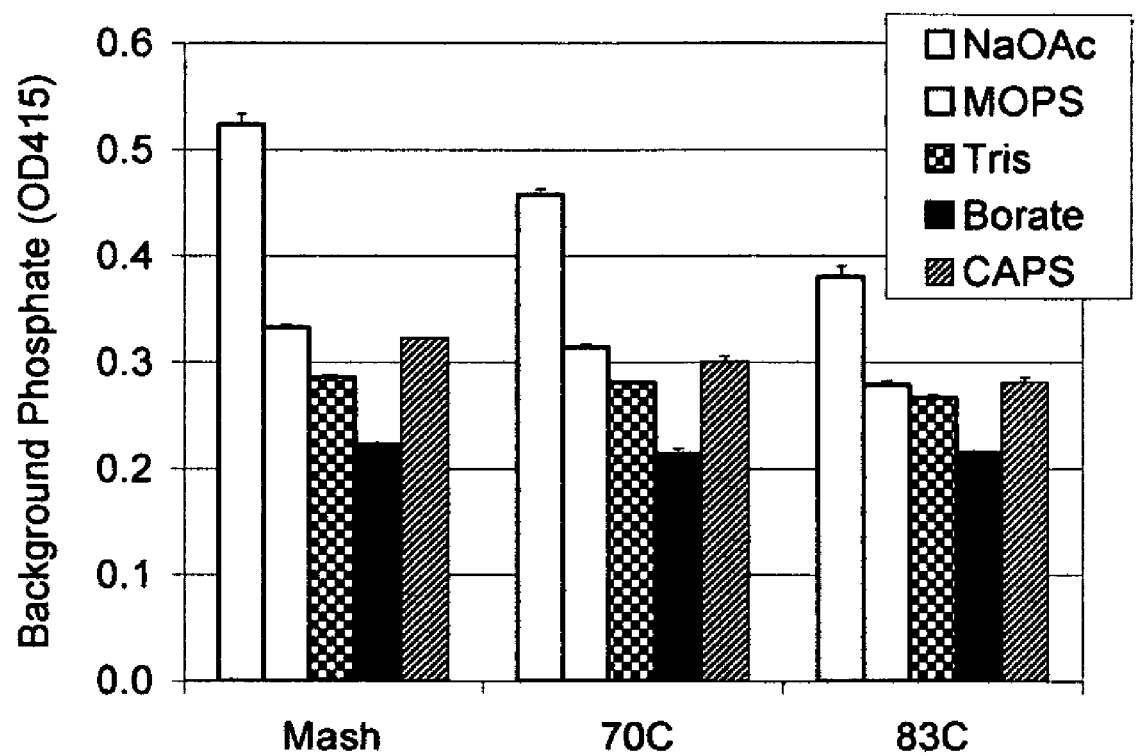
FIG. 2 is a graph showing that the concentration of background phosphate of feed extracts was dependent on extraction buffer and pH. Buffer concentrations were all 25 mM TWEEN 20 was not added. NaOAC, sodium acetate; Tris, Tris-HCl; borate, sodium borate.

A preferred phytase extraction buffer would also minimize the extraction of endogenous or background phosphate from feed samples. Whether supplemented with phytase or not, feeds for monogastric animals are still fortified with inorganic phosphate typically in the form of monocalcium phosphate or dicalcium phosphate. This inorganic phosphate component in the feed, in addition to phosphate present in the vegetable components of the feed, is not distinguishable from phosphate liberated by phytase activity during an enzymatic assay. Therefore it is advantageous to minimize the concentration of phosphate extracted from feed while maximizing the concentration of phytase extracted. Achieving a low concentration of background phosphate relative to the phytase concentration in a feed extract results in a higher signal-to-noise ratio for the phytase activity assay. As shown in FIG. 2, the sodium borate at pH 10 recovers more phytase activity from pelleted feed compared to other buffers at pH 5 (NaOAC), 7 (MOPS), 8 (Tris), and 10 (CAPS). 70° C. and 83° C. refer to feed conditioning and pelleting temperature.

FIG. 2 also shows the sodium borate pH 10 buffer extracted less endogenous or background phosphate from the milled feed samples compared to the other four buffers tested. Also the sodium borate pH 10 buffer extracted the same amount of endogenous phosphate from each of the three feed sample types (mash, 70° C. pellets, 83° C. pellets). By contrast the concentration of background phosphate in the pH 5, pH 7, and pH 10 extracts was highly variable depending on the feed sample type. Consistency in the concentration of endogenous phosphate extracted is critical to achieving accurate and reproducible phytase assay results, especially when the enzyme is present at very low concentrations as in these animal feed samples.

Comparison of Sodium Borate pH 10 Buffer and AOAC Dilution Buffer

Figure 3:
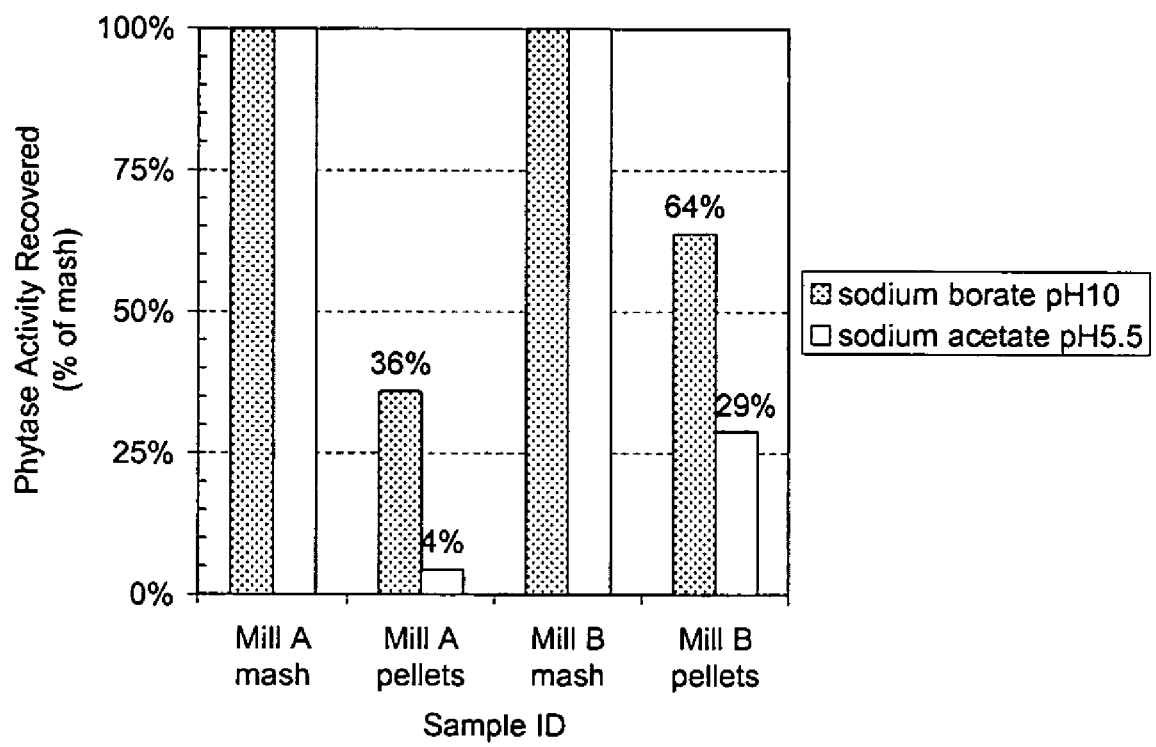
FIG. 3 is a graph showing that the sodium borate pH 10 buffer with 0.01% TWEEN 20 extracts phytase activity more efficiently from pelleted feed compared to AOAC Dilution Buffer (250 mM sodium acetate pH 5.5, 0.01% TWEEN 20, 1 mM $CaCl_2$). Feed batches were mixed, conditioned, and pelleted at two different mills (Mill A and B), and feed batch samples were processed and sub-samples were analyzed in triplicate for phytase activity as described in Example 3. Phytase activity recovered is expressed as a percent of the activity recovered from the corresponding mash sample (same mill, same batch) using borate extraction buffer (pH 10).

Additional confirmation that the 25 mM sodium borate pH 10 buffer is an efficient phytase extraction buffer for use with pelleted feed is presented in FIG. 3. Mash and pelleted feed samples containing QUANTUM Phytase 2500D were obtained from two research mills designated A and B. Feed conditioned at high temperatures was chosen for this comparison in order to emphasize the superior efficacy of the borate buffer at extracting phytase activity from pelleted feed. In this experiment replicate subsamples of the same milled feed samples were extracted in either the borate buffer or a buffer consisting of 250 mM sodium acetate pH 5.5 and 0.01% TWEEN 20. This buffer is the Dilution buffer described in AOAC Official Method 2000.12 Phytase Activity in Feed. We will refer to this buffer as AOAC Dilution Buffer. All extracts were then diluted further with AOAC Dilution Buffer. Diluted borate extracts were assayed at pH 4.5 and 60° C. and diluted sodium acetate extracts were assayed at pH 5.5 and 37° C. As shown in FIG. 2, the borate pH10 buffer extracted about twice the amount of phytase activity from pellets manufactured at mill B compared to the AOAC Dilution Buffer. The difference between extraction buffers was more striking for feed manufactured at mill A. In this case use of the borate pH 10 buffer resulted in recovery of nine times as much phytase activity from pelleted feed (relative to mash) compared to the AOAC Dilution Buffer.

Comparison of Sodium Borate pH10 Buffer and AOAC Feed Buffer

A similar analysis was performed using feed samples manufactured at mill C. In this case sub-samples of milled feed samples were extracted using 25 mM sodium borate pH 10 buffer and a buffer consisting of 250 mM sodium acetate pH 5.5, 0.01% TWEEN 20, and 68.4 mM $CaCl_2$. This buffer is the Feed extraction buffer described in AOAC Official Method 2000.12 Phytase Activity in Feed. We will refer to this buffer as AOAC Feed buffer.

Figure 4:
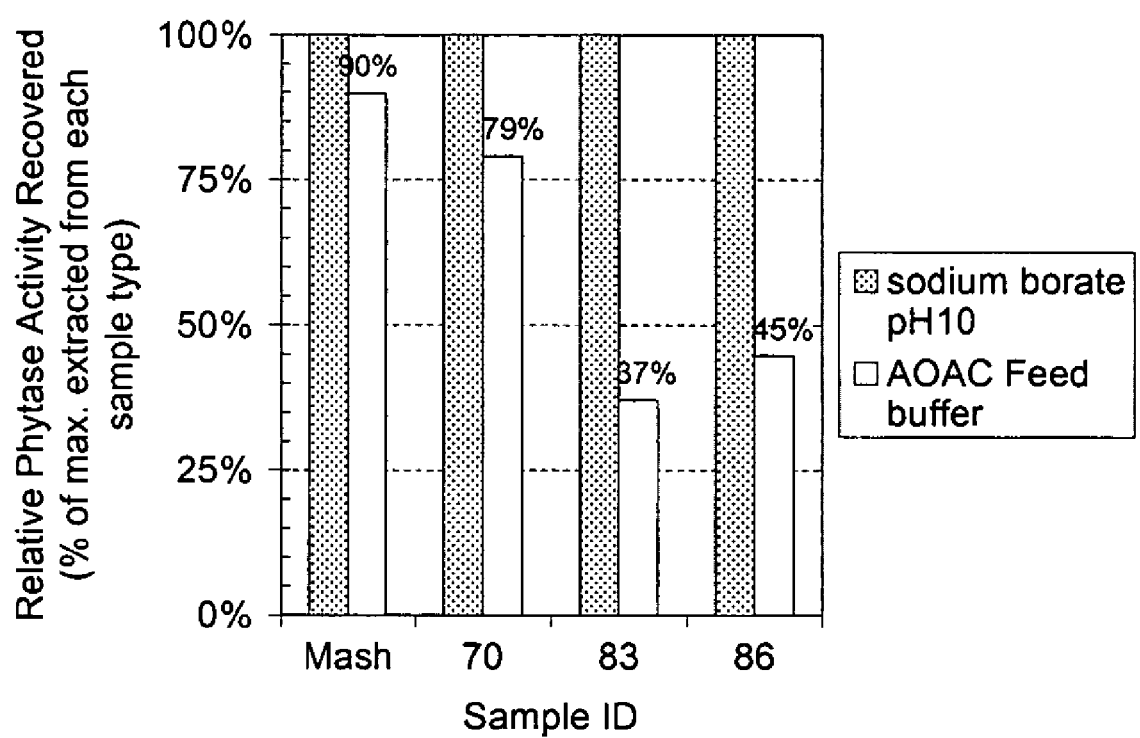
FIG. 4 is a graph showing sodium borate pH 10 buffer with 0.01% TWEEN 20 extracts phytase activity more efficiently from pelleted feed compared to AOAC Feed buffer (250 mM sodium acetate pH 5.5, 0.01% TWEEN 20, 68.4 mM $CaCl_2$). Feed batches were mixed, conditioned, and pelleted at feed mill C, and feed batch samples were processed and sub-samples were extracted as described in Example 3. Extracts of milled feed samples were diluted with AOAC Dilution buffer and assayed at pH 5.5 and 37° C. to determine FTU/kg feed. The mash sample extracted with sodium borate pH 10 buffer contained 871 FTU/kg, and the samples pelleted at 70° C., 83° C., and 86° C. contained, respectively, 68%, 23%, and 13% of this initial activity. Phytase activity is expressed as the percent of enzyme activity recovered from each type of sample extracted with borate buffer (pH 10).

FIG. 4 shows that the sodium borate pH 10 buffer was more efficient than the AOAC buffer at extracting phytase activity from all feed sample types. Most notably the borate buffer extracted more than twice the phytase activity extracted by the AOAC Feed buffer from feed that had been conditioned and pelleted at the higher temperatures of 83° C. and 86° C.

Comparison of Fully Optimized Method Described here and AOAC Official Method 2000.12

Figure 5A:
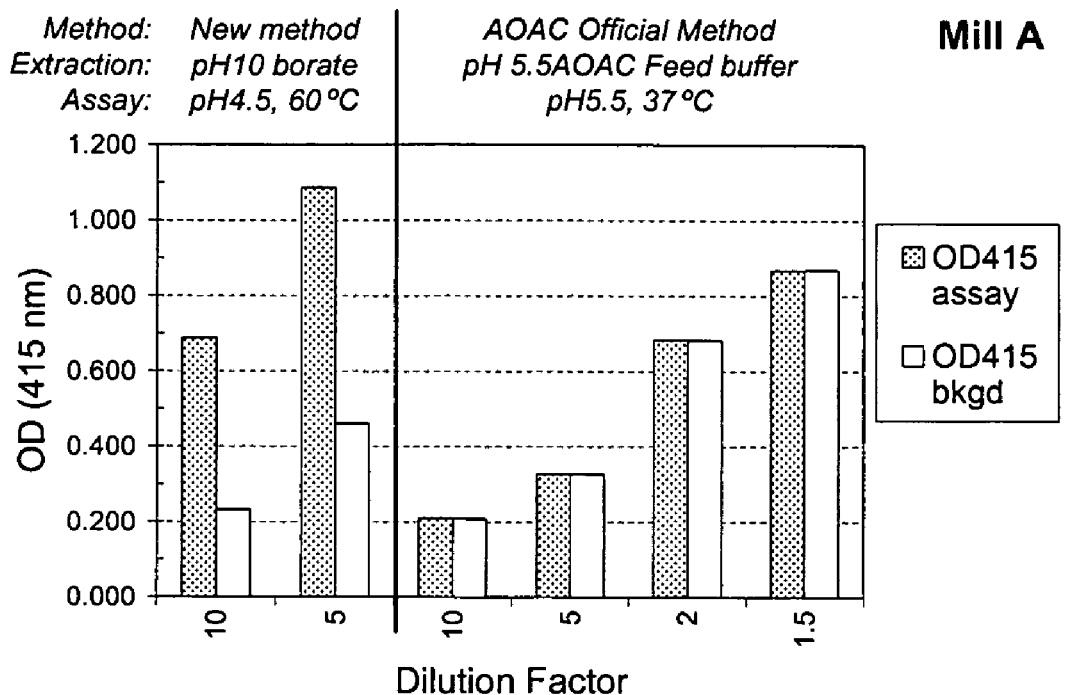
FIGS. 5A and B are graphs comparing the AOAC method and the phytase method of this application. AOAC Official Method 2000.12 underestimates phytase activity in pelleted feed containing QUANTUM Phytase 2500D. Pelleted feed samples from mill A (FIG. 5A, top) and mill D (FIG. 5B, bottom) were milled and sub-samples were extracted either according to the method described here (extraction in sodium borate pH 10 buffer and dilution and assay at pH 4.5, 60° C.) or according to the AOAC Official Method 2000.12. The sample contained about 200 FTU/kg measured according to the new method and using a conversion factor of 5.66 units=1 FTU. The figure shows the plot of the measured absorbances (at 415 nm) after addition of the color-stop reagent to the reaction assay and the background (bkgd) mixture. Note that the pH of the reaction mixture for pH 10 borate buffer extracted enzyme could not be shifted to pH 4.5 (for phytase assay) by less than 5 fold dilution of the extract.
Figure 5B:
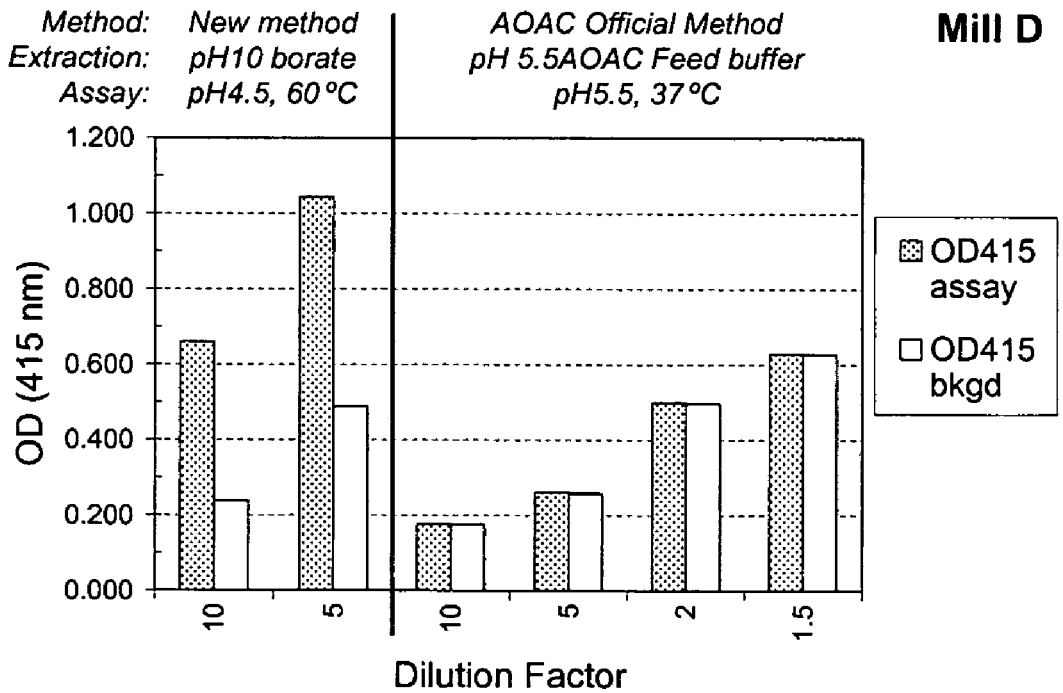

The AOAC Official Method 2000.12 does not detect phytase activity in some pelleted feed samples that contain significant levels of phytase added pre-pelleting. Pelleted feed samples from mills A and D were analyzed either using the method described here or using the AOAC Official Method 2000.12. The optical density values of the enzyme reactions for phytase activity and background phosphate are summarized in FIGS. 5A and B. Using the new method with dilution of borate pH 10 extracts either 10-fold or 5-fold in pH 4.5 dilution buffer resulted in a signal-to-noise ratio of >2 for samples from mills A and D. By contrast using the AOAC Official Method no phytase activity was detected above background phosphate levels in extracts diluted from 10-fold to as low as 1.5-fold in preparation for activity assay.

Example 6

Efficient Extraction of Phytase from Transgenic Corn Flour using the Borate Buffer described in Example 1 is Required for Activity Assay Accuracy Compare Extraction pH 5.5, 8, 10 Using Flour of Transgenic Corn Expressing Phytase Commercially available recombinant feed enzymes are all produced in microbial expression hosts. However, transgenic crops represent an alternative method for producing recombinant feed enzymes. The production of a thermotolerant *E. coli*-derived phytase in corn seed was described recently in (U.S. Patent Application Publication No. 2003-0170293).

One advantage to producing feed enzymes in corn seed is that the equivalent of existing dry product formulations can be manufactured simply by grinding the corn. Commercially available dry product formulations may consist of enzyme dried onto a bulking agent or carrier such as wheat mids. Alternatively the enzyme may be embedded in the bulking agent, for example in an extruded granule-type formulation. The phytase expressed in corn seed is naturally embedded in the bulking agent, which in this case consists of the individual cells of the seed endosperm tissue.

Figure 6A:
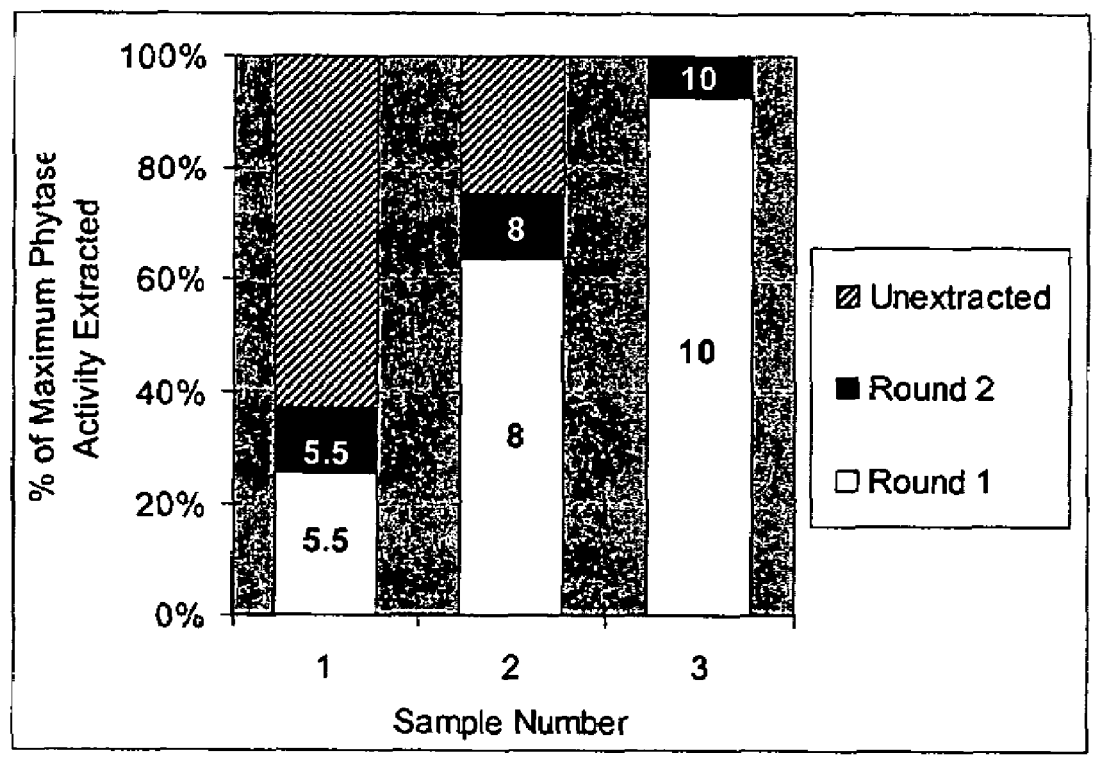
FIGS. 6A and B show results from a sequential extraction of transgenic corn seed flour with different buffers. Sample "5.5" is AOAC Dilution buffer (250 mM sodium acetate pH 5.5, 1 mM $CaCl_2$, 0.01% TWEEN 20). Sample "8" is 50 mM Tris-HCl pH 8.0, 100 mM NaCl, 2 mM EDTA. Sample "10" is 25 mM sodium borate pH 10, 0.01% TWEEN 20.
Figure 6B:
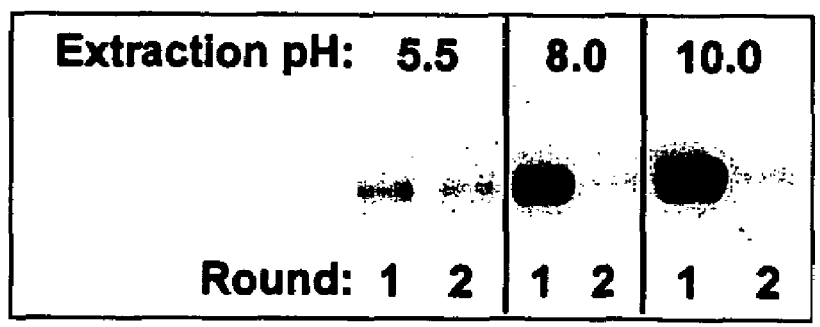
FIG. 6B is a Western blot analysis of extracts analyzed in FIG. 6A.

Commercialization of a phytase enzyme formulated as milled transgenic corn will require efficient extraction of the enzyme from corn flour for accurate measurement of enzyme concentrations. We tested the extraction efficiencies of the sodium borate Ph 10 buffer with 0.01% Tween™ 20 described in Example 3, a buffer consisting of 50 mM Tris-HCl pH 8.0, 100 mM NaCl, and 2 mM EDTA, and the AOAC Dilution Buffer described above (250 mM sodium acetate pH 5.5, 1 mM $CaCl_2$, 0.01% TWEEN 20). Replicate 1-gram samples of transgenic corn flour containing endogenous recombinant phytase were extracted sequentially. Extracts were diluted with AOAC Dilution Buffer and phytase activity of the diluted extracts was measured at pH 5.5 and 37° C. The results are shown in FIG. 6. The AOAC Dilution Buffer, which is the standard buffer used to extract phytase activity from commercially available dry product formulations, does not efficiently extract phytase from milled transgenic corn flour. This buffer extracted <30% of the phytase activity extracted by the sodium borate pH buffer. This buffer therefore is not an acceptable extraction buffer for use with a corn seed-expressed phytase. The results in FIGS. 6A and B further demonstrate that the sodium borate pH 10 buffer with TWEEN 20 (0.01%) extracts more than 90% of the total extractable phytase activity in the first of two sequential extractions.

Efficient Extraction with Borate pH 10.0 Confirmed by Western Blotting

The result described in the above section and shown in FIG. 6 does not, however, rule out the possibility that additional recombinant phytase protein, active or inactive, remains in the extracted flour and is resistant to extraction in this buffer. In order to confirm that the sodium borate pH 10 buffer with Tween™ 20 extracts all or nearly all of the recombinant phytase protein another series of sequential extractions was performed. In this experiment 0.4-gram samples of transgenic corn flour were extracted sequentially in 1-3 rounds with either the sodium borate pH 10 buffer supplemented with Tween™ 20 or with a denaturing buffer that was developed for extraction of total protein from corn seed, including the highly insoluble prolamin protein fraction. This denaturing extraction buffer, which we will refer to as Total Protein Extraction Buffer (TPEB) consists of 12.5 mM sodium borate (pH 10), 1% SDS, and 2% 1-mercaptoethanol (Wallace, et al., Plant Physiology 92:192-96, 1990).

Replicate samples of transgenic corn flour and a single sample of control (non-transgenic) corn flour were extracted with borate pH 10 buffer. These first-round extracts are shown in the Western blot in FIG. 7 (lanes 1, 4, 6, 9, 11, 14, 17). First round pellets were washed once with ice-cold water. All extracts contain a single prominent band of about 45 kD as predicted for the corn-expressed phytase described in (Lanahan and Betts, U.S. Patent Application Publication no. 2003-0170293).

The first round borate pellets were then re-extracted either with borate buffer or with denaturing TPEB, and the second round borate pellets were washed with water and re-extracted with TPEB. These extracts were also analyzed in the Western blot shown in FIG. 7. No additional immunodetectable phytase was present in the round 2 and round 3 extracts (lanes 2, 3, 5, 7, 8, 10, 12, 13, 15, 16) at the level of sensitivity of this blot.

Figure 7:
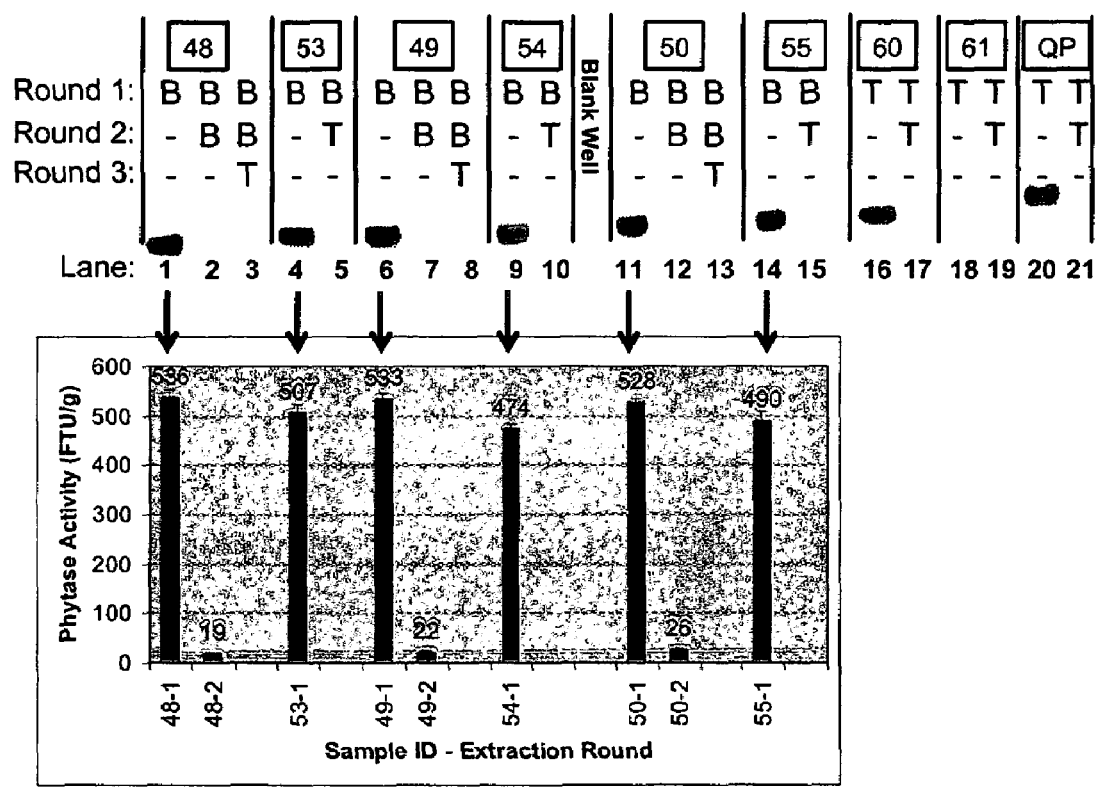
FIG. 7 is a photograph of a Western blot and a graph showing that sodium borate pH 10 extraction buffer with 0.01% TWEEN 20 extracts >95% of total recombinant phytase activity (and recombinant phytase protein) from milled corn flour. Corn flour samples were extracted in 1-3 rounds with buffer B and buffer T. Buffer B consisted of 25 mM sodium borate (pH 10), 0.01% Tween™ 20. Buffer T (Total Protein Extraction Buffer) consisted of 12.5 mM sodium borate pH 10, 1% SDS, 2% 1-mercaptoethanol. Top: Western blot analysis of all extracts. Transgenic corn flour: samples 48, 53, 49, 54, 50, 55, and 60. Non-transgenic corn flour: sample 61. QP, QUANTUM Phytase 2500D extract. Bottom: Phytase activity of buffer B extracts only. Note that after extraction with the denaturing buffer TPEB, phytase activity was not assayed.

All round 1 and round 2 extracts in sodium borate pH 10 buffer were also analyzed for phytase activity as shown in the chart in FIG. 7. The average phytase activity of the round-1 borate pH 10.0 extracts was 505±38 FTU/g (includes additional replicates not shown in the figure). Five replicate transgenic corn flour samples were sequentially extracted with borate buffer (only three are shown in the figure, samples 48, 49, 50). The average phytase activity of the five round-1 borate extracts was 509 FTU/g, and the average activity of the five round-2 extracts from the same set of pellets was 23 FTU/g. This residual phytase activity extracted in round 2 was not detected by Western blot analysis at the level of sensitivity of this blot. The total phytase activity extracted (sum of round 1 and round 2) was, on average, 531 FTU/g, with 95.8% of the activity extracted in round 1. This result demonstrates that the borate pH 10 buffer with 0.01% Tween™ 20 used is 95-96% efficient at extracting phytase activity in a single 60-min extraction of transgenic corn flour with continuous agitation at room temperature.

Extension of Method to Additional Recombinant Proteins Expressed in Transgenic Corn Seed The ability of the sodium borate pH 10 buffer to extract other recombinant enzymes efficiently from corn flour was tested. Samples of transgenic corn seed containing recombinant cellulase and recombinant amylase were extracted at pH 10 (25 mM sodium borate pH10, 0.01% Tween™ 20) and pH 5.5 (250 mM sodium acetate pH5.5, 0.01% Tween™ 20). Extracts were diluted and analyzed by ELISA. The results are summarized in FIG. 8. Corn flour samples containing the same recombinant phytase analyzed in FIGS. 6 and 7 were included in the experiment for comparison. The pH 5.5 buffer extracted 32%, 0%, and 66% of the phytase, amylase, and cellulase proteins, respectively, that were extracted by the borate pH 10 buffer.

Example 7

Pulverization of Feed Enzyme Dry Product when Present in Feed at Commercial Inclusion Rates is Required for Acceptable Activity Assay Precision Particulate feed enzyme products are added to mash (unpelleted) feed at extremely low inclusion rates. For example QUANTUM Phytase 2500D is recommended to be added to broiler diets at 200 grams of product per metric ton of feed. Development of an accurate, precise, and practical analytical method for enzyme activity in feed requires the availability of uniform and representative feed samples. A typical commercial batch size for animal feed may be 5 or 10 tons. Convenient samples for analysis are <1 kg and preferably smaller. The AOAC Official Method 2000.12 specifies that a feed sample of 100-150 grams is milled to <1 mm particle size and then duplicate sub-samples of 5 grams each are analyzed. Therefore to achieve accurate and precise measurement of phytase activity using this official method the initial 100-150 gram batch sample must be representative of the full multi-ton batch. Furthermore the small 100-150 gram batch sample must be highly homogeneous and well-mixed so that the duplicate 5 gram sub-samples yield similar results.

In our early analytical method development work for Quantum™ Phytase dry product we used sample sizes and sample processing methods consistent with those specified in the AOAC Official Method 2000.12. These methods consistently generated activity assay results with unacceptably high variation across both replicate sub-samples and replicate batch samples. This result implicated batch sample heterogeneity as the cause of the variability in activity assay measurements.

In order to better understand the distribution of Quantum™ Phytase 2500D product particles within feed samples we analyzed individual feed pellets for the presence of the QUANTUM Phytase protein using an ELISA. As shown in Table 3, QUANTUM Phytase was detected in about one third of feed pellets from a batch containing QUANTUM Phytase 2500D at the recommended inclusion rate of 200 grams per metric ton. The fraction of pellets containing one or more particles of QUANTUM Phytase 2500D increased to about 50% as the inclusion rate of the product increased to 400 grams per ton (Table 5).

TABLE 5

At recommended product inclusion rate, most pellets do not contain product. A sample of feed pellets containing Quantum ™ Phytase 2500D at inclusion rates of 200 and 400 grams per metric ton of feed were analyzed individually for the presence of Quantum ™ Phytase protein.

| Product Inclusion Rate | Enzyme | # pellets | PELLET WEIGHTS (mg) | | ELISA RESULT (# pellets) | | | |
|---|---|---|---|---|---|---|---|---|
| (mg/kg) | Dose (FTU/kg) | analyzed | AVE | SD | POS | NEG | SUM | % POS |
| 200 (recommended) | 500 | 134 | 160 | 42 | 42 | 92 | 134 | 31% |
| 400 | 1000 | 103 | 174 | 45 | 52 | 51 | 103 | 50% |

The average feed pellet from these batches weighed about 170 mg. Therefore a 5-gram sub-sample would be derived from, on average, about 30 pellets (10 pos. and 20 neg.). Also a batch sample of 100-150 grams of feed would contain, on average, from 600 to 900 pellets total. Because as demonstrated in Table 4 most of these pellets are not expected to contain particles of the enzyme product, the potential for sample heterogeneity is high and will depend on the attention paid to sample collection and sample dividing at every step prior to analysis.

Figure 9:
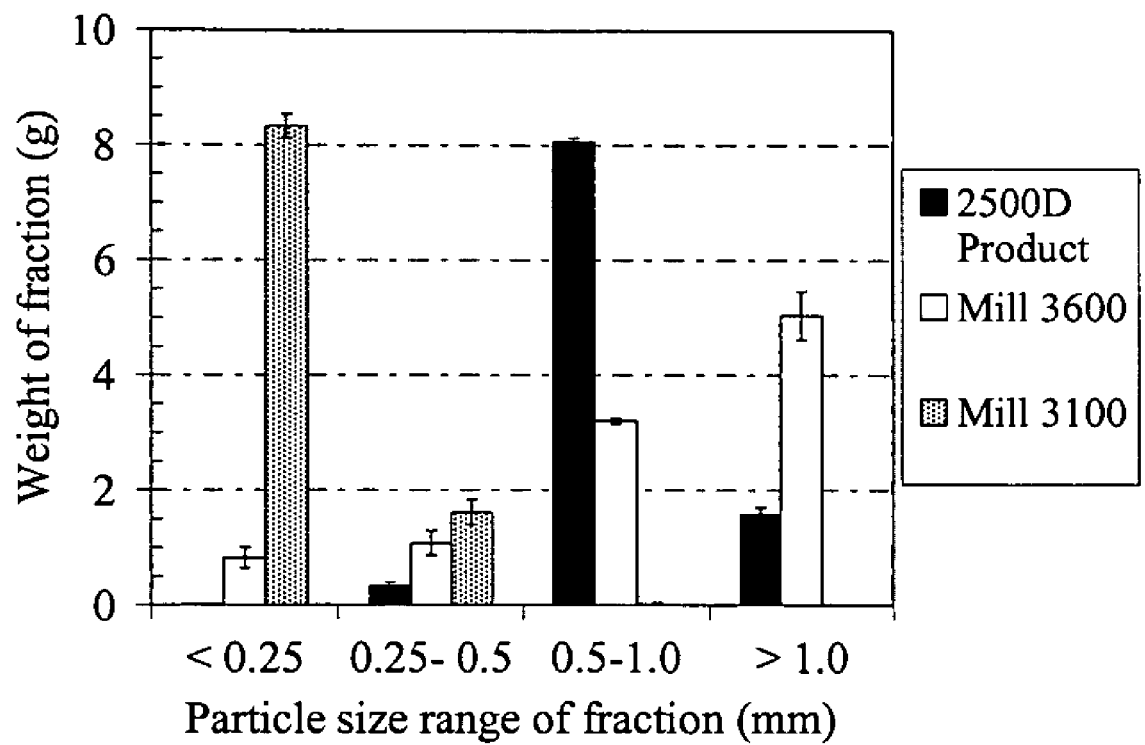
FIG. 9 is a graph showing particle size analysis of QUANTUM Phytase 2500D dry product (unmilled) and pellet feed samples milled using a hammer mill (Laboratory Mill 3600, Perten Instruments with 0.8 mm screen) and disc mill (Laboratory Mill 3100, Perten Instruments with disc #1 at setting 0).

A major challenge to establishing a routine analytical capability for a commercial product support service is ensuring that every sample submitted for analysis is thoroughly mixed according to the standard procedure. In practice however this is often not the case as with any highly routine and repetitive manual procedure. We therefore tested the idea that we could generate a more homogeneous and uniform feed batch sample by increasing the concentration of enzyme product particles in the feed batch sample. This could be achieved by pulverizing the feed batch sample to a small average particle size. For this experiment we compared two milling methods for processing replicate feed batch samples of about 300 grams. The first method used a disc-type mill (Laboratory Mill 3600, Perten Instruments), which as used functions primarily to mix mash feed samples and to break up and mix pellet samples. Here we refer to the Laboratory Mill 3600 as a disc mill. The second method used a beater or hammer-type mill (Laboratory Mill 3100, Perten Instruments), which as used with a 0.8 mm screen efficiently pulverized feed components, including the enzyme dry product, to <500 microns. Here we refer to the Laboratory Mill 3100 as a hammer mill. FIG. 9 shows the particle size distribution of a sample of QUANTUM Phytase 2500D and of milled feed samples. QUANTUM Phytase 2500D is almost all >0.5 mm. The feed sample milled with the disc mill (3600) consists primarily of particles >0.5 mm. By contrast the hammer mill (3100) pulverized the feed particles to mostly <0.25 mm. These results demonstrate that grinding feed samples using the hammer mill further reduces the particle size of all feed components, including the enzyme dry product. The consequence of this pulverization step is that the number of particles of feed enzyme dry product per unit sample of feed increases.

Figure 10:
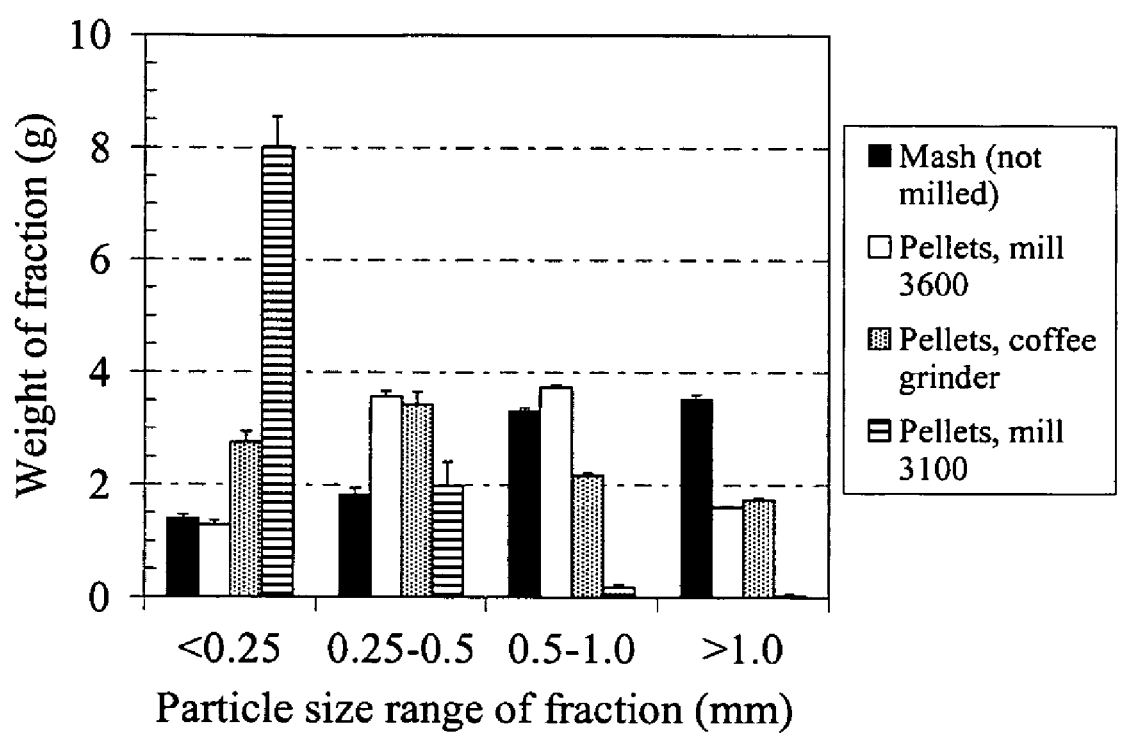
FIG. 10 is a graph comparing particle size analysis of mash feed (unmilled) and milled feed pellets. Laboratory Mill 3600 (Perten Instruments); disc mill with disc #1 at setting 0. Laboratory Mill 3100 (Perten Instruments); hammer mill with 0.8 mm screen. Coffee grinder, Kitchen Aid Model BCG100WH1. Each bar represents the average of 9 fractionations: three 50-gram samples were milled and from each of these three 10-gram sub-samples were fractionated.

Coffee grinders are commonly used to mill feed batch samples for convenience. Additional grinding tests were performed to compare the particle size profiles of mash feed (unmilled) and pelleted feed milled using the disc mill, coffee grinder, and hammer mill. The results are shown in FIG. 10. In this experiment the coffee grinder achieved a particle size range intermediate to the hammer mill and disc mill. The hammer mill was the only of the three mills that generated particles that were predominantly <0.25 mm.

Figure 11A:
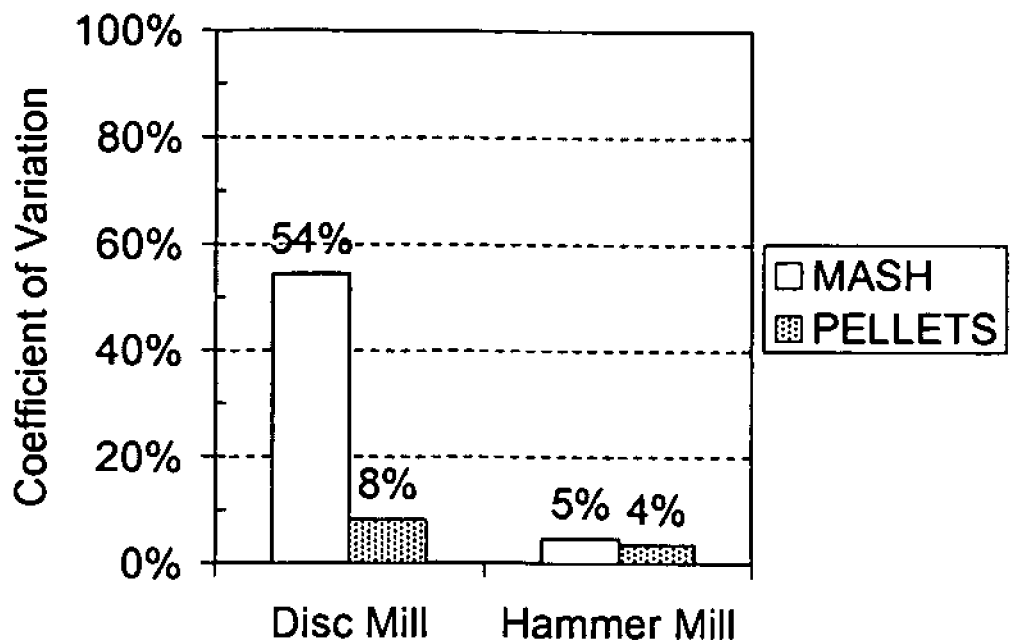
FIGS. 11A and B are graphs showing the variability of phytase activity recovered across 10 sub-samples taken from a single milled feed batch sample of mash feed and of pelleted feed. The experiment was performed twice.
Figure 11B:
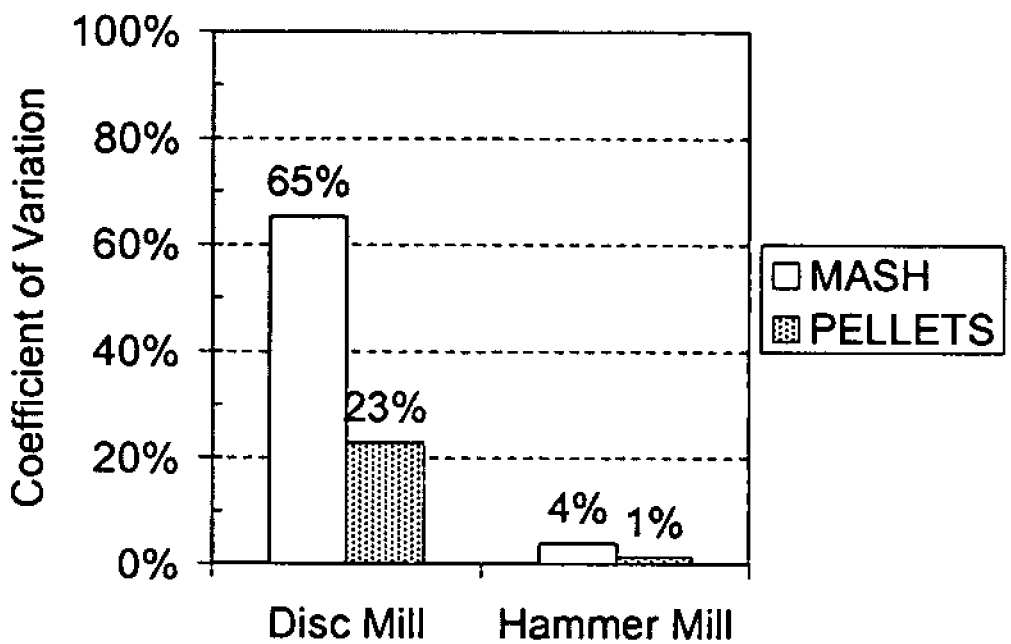
FIG. 11B: Rep 2.

We next investigated if these differences in sample (and product) pulverization had the intended effect of increasing the homogeneity and uniformity of feed batch samples. The results of a typical experiment are shown in FIG. 11.

In this experiment duplicate samples of mash feed and duplicate samples of pelleted feed were milled using a disc mill and a hammer mill as described above and in FIG. 9 and FIG. 10. Ten replicate sub-samples were extracted and analyzed for phytase activity as described in Example 3. The coefficient of variation (CV) of the phytase activity measurement across the 10 samples (defined as inter-assay CV or the variability across replicate extractions) was determined for each of the four milled samples. The experiment was performed twice and the results are plotted in panels A and B. In both experiments the inter-assay CV was higher when samples were milled using a disc mill compared to a hammer mill. Also mash samples processed on the same mill type gave consistently higher inter-assay CV. These results demonstrate the importance of sample pulverization with a hammer mill to generate a uniform feed batch sample that can be sub-sampled for accurate enzyme analysis.

Figure 12A:
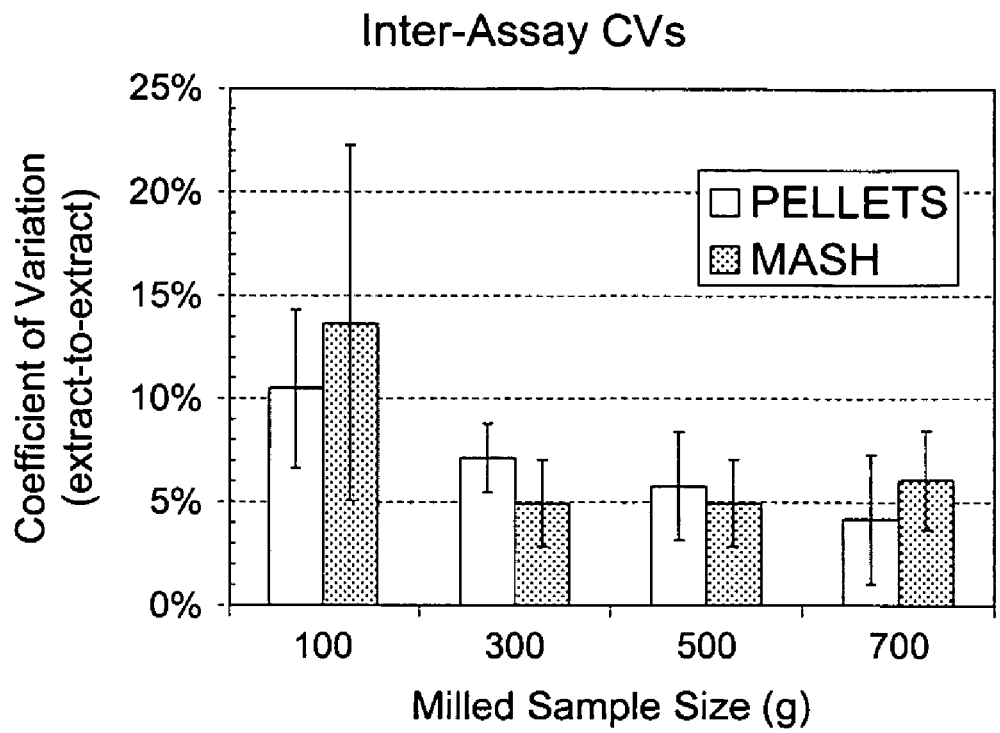
FIGS. 12A and B show the effect of size of feed batch sample on variability of enzyme activity recovered from mash and pelleted feed. Milled samples were analyzed for phytase activity according to the procedure described in Example 3.
Figure 12B:
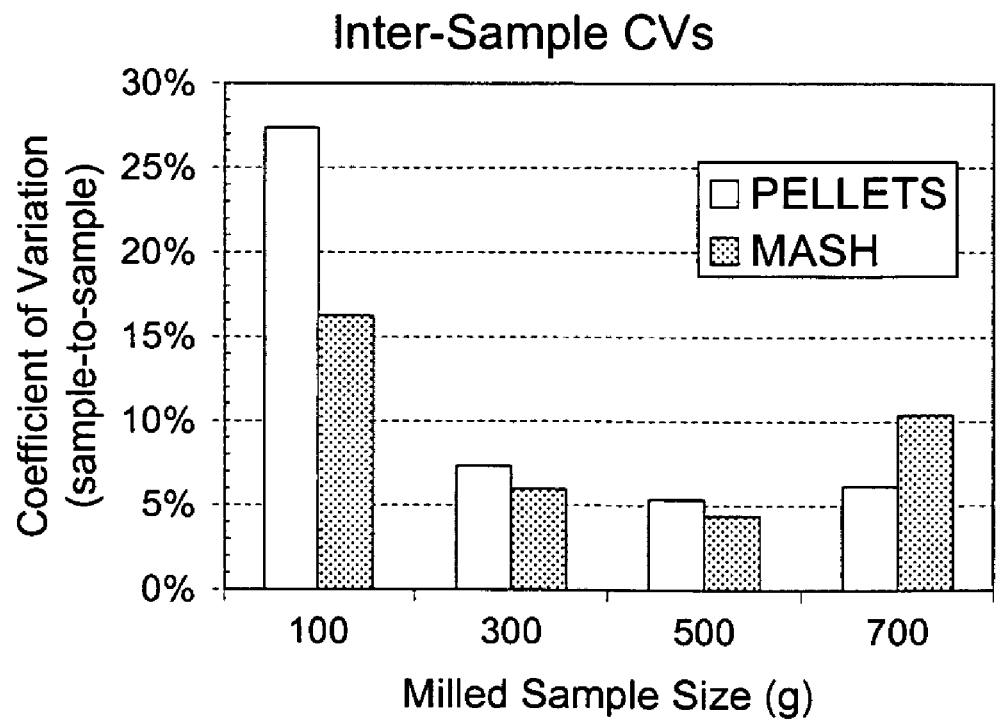

In another series of experiments we determined that the optimal feed batch sample size for hammer milling is >10 g. The experiment summarized in FIG. 12 shows that a batch sample size of 100 g results in unacceptably high variability in phytase activity measurements of replicate milled samples. In other words a 100 g milled sample is not reliably representative of the complete feed batch. Samples (10 kg) of mash feed and pelleted feed treated with Quantum™ Phytase 2500D at an inclusion rate of 200 g per tonne were obtained from mill F. The 10-kg sample was mixed thoroughly and smaller samples of 100 g, 300 g, 500 g, and 700 g were removed in triplicate. These sub-samples were ground according to the milling procedure described in Example 1. Each milled sub-sample was extracted in triplicate and each extract was assayed in triplicate according to the procedure outlined in Example 3. FIG. 12A shows the average inter-assay CVs for the 4 sets of milled samples. The phytase activity measurement was highly reproducible (CV <10%) across replicate extractions when the milled sample size was >100 g. FIG. 12B shows the CVs of the phytase activity measurements (not shown) as a function of milled sample size. This is the assay variability from milled sample to milled sample, defined here as the inter-sample CV. The results demonstrate that the reproducibility of the phytase measurement is unacceptably low when a batch sample of 100 g was used (CV>15% for mash and pellets). Milled batch samples of 300, 500, and 700 grams yielded acceptable inter-sample CVs (<15%).

Example 8

Determination of Extractable Phytase Enzymatic Activity from Corn Seed and Milled Corn at pH 5.5 by Inorganic Phosphate Release This assay is based on the detection of inorganic phosphate released from sodium phytate substrate by the hydrolytic enzymatic action of phytase. Sodium phytate substrate and phytase enzyme are incubated for 60 minutes at 37° C., followed by simultaneous reaction quenching and colorimetric detection. Color formation, which is measured spectrophotometrically at 415 nm, is the result of molybdate and vanadate ions complexing with inorganic phosphate.

2.0 Unit Definition. One phytase unit (FTU) is the quantity of enzyme that liberates 1 µmol of inorganic phosphate per minute from sodium phytate at 37° C., pH 5.5, under standard assay conditions.

Materials, Chemicals and preparation of solutions are as described above in Example 2.

Sample Preparation. Milling. Grind 50 g of well mixed corn seed or milled corn (test article) in a Perten 3100 Hammer Mill using a screen with $\leq$0.8 mm pore size. If the mill is heating up, allow the mill to cool down between each grinding. Mix well after milling and before removing milled samples for analysis. It is recommended that the sample size for milling be 50 g. Note that, if the sample size is greater that 50 g, the sample should be mixed extremely well before the 50 g aliquot is taken out of the sample for grinding in the Hammer Mill.

Controls/Standards. Prepare a batch of Quantum™ 2500D for use as a control by milling a 50 g sample as described above. After milling, mix well before removing samples. Include a set of controls with each assay. OPTIONAL. For a negative control, use milled corn (with no phytase (blank seed)). Milled Quantum Phytase 2500D. Add 0.40 g Quantum 2500D (milled as described above) to a 100 mL volumetric flask followed by borate extraction buffer up to 100 ml. On the dilutions sheet enter a sample weight of 1.0 g for this sample. OPTIONAL. For a positive control of dry Quantum in corn flour, mix 400 mg of Quantum 2500D with 600 mg negative corn flour in a 100 ml volumetric flask followed by borate extraction buffer up to 100 ml (assuming an activity of 1,000 FTU/g). OPTIONAL. Liquid Quantum Phytase. For the Quantum liquid standard, dilute a liquid Quantum™ sample with a concentration of 15,000 FTU/g 1:15 (200 ul 15,000 FTU/g+2.8 ml Sodium acetate buffer, pH 5.5). Alternatively a sample of 5000 L with a concentration of >5000 FTU/g is diluted 1:5 (600 ul 5000 L+2.4 ml Sodium acetate buffer, pH 5.5). Record all dilutions. Add 1,000 FTU (1 ml) of the diluted laboratory stock of liquid QUANTUM Phytase (1,000 FTU/g) to a 100 ml volumetric flask and fill up to 100 ml with Sodium borate extraction buffer. On the dilutions sheet for this sample enter a sample Weight of 1.0 g. The above control extracts will be diluted the same as a corn phytase Dry product with an expected activity of 1,000 FTU/g.

Sample Extraction and Dilution Preparation

Dry Product Extraction. The extraction is carried out in a 100 ml volumetric flask. On a tared balance measure and record the mass of the 100 mL wide-neck volumetric flask(s). Weigh approximately 1.0 gram (+/−0.05) of corn phytase dry product and add to the pre-weighed 100 ml volumetric flask (s). Weigh and record the weight of the 100 ml volumetric flask with the 1.0 g of corn phytase added. Add 25 mM sodium borate extraction buffer, pH 10.0 up to the mark in the flask. Reweigh the full flask and record the final mass. Add a magnetic stirring bar to the flask, taking care not to let liquid spill as the stirring bar is being added, then place onto a magnetic stirrer and extract for 60 minutes at room temperature (~22° C.). Wash any corn particles stuck to the neck of the flask down into the bulk liquid by inverting the flask a few times prior to starting the extraction. A vigorous rate of stirring should be used throughout the extraction procedure. The solution will attain a milky, cloudy appearance. Following the 60 minute incubation, remove the flask and pour pipette 10 ml into a 16×100 glass test tube and centrifuge for 10 minutes at 2,000 g. Proceed to the dilution. Three replicates should be conducted for each batch of dry phytase product being analyzed.

Determination of the Total Mass of Buffer Used in the Extraction Protocol:

Subtract the mass of dry phytase product plus the mass of the empty flask from the mass of the flask with the solids and buffer contents. This quantity will be in units of grams (g).

Primary Dilution of Extract. One glass tube will be required for each sample extracted. Tare the balance with the empty tube on it, and then add 0.5 mL of the dry product 1× extract. Record the mass of added extract. Add 4.5 ml 250 mM sodium acetate buffer and weigh the tube once more (this will be the total mass of the liquid). Record all measurements. Vortex the tube containing the primary dilution thoroughly.

Calculation of the Primary Dilution Factor: Take the mass of the added 1× extract (approximately 0.5 g) and divide it by the total mass of liquid in the tube (approximately 5.0 g). The inverse of this value is the primary dilution factor. It will be approximately 10 based upon mass.

Secondary Dilution of Extract. One glass tube will be required for each sample diluted. Tare the balance with the empty tube on it, and then add 0.5 mL of the dry product extract 1:10 dilution. Record the mass of added extract. Add 4.5 ml 250 mM sodium acetate buffer and weigh the tube once more (this will be the total mass of the liquid). Record all measurements. Vortex the tube containing the secondary dilution thoroughly.

Calculation of the Secondary Dilution Factor: Take the mass of the added 1:10 diluted extract (approximately 0.5 g) and divide it by the total mass of liquid in the tube (approximately 5.0 g). The inverse of this value is the secondary dilution factor. It will be approximately 10 based upon mass. The total dilution is 1:100.

Assay Working Dilution. As corn phytase dry products of varying phytase concentrations will be encountered during the course of this assay, a rapid range finder study may be required to determine the optimal dilution rate to get a particular sample analysis onto scale. The range finder study is conducted by preparing the dry product extract and the primary and secondary dilutions. Variations to this assay are then made with regards to the preparation of the working dilution listed below.

For the range finder study a set of working dilutions is made on a volumetric basis, and these are then run through a modified corn phytase assay. The range finder assay may be run with only a single reaction tube for each dilution to be tested and with no reaction blanks. Once the optimal dilution rate has been determined, continue the assay by preparing the determined working dilutions. The target absorbance at 415 nm is between 0.4 and 1.1. For corn phytase dry product in the 1,000 FTU/g range, a working dilution of approximately 1:500 will produce an absorbance reading that is on scale. Corn phytase dry product at 1,000 FTU/g at a 1:500 dilution should have a 415 nm absorbance reading of approximately 0.5

One glass tube will be required for each diluted sample. Tare the balance with the empty tube on it, and then add 1.0 mL of the 1:100 diluted dry product. Record the mass of added diluted extract. Add 4.0 ml 250 mM sodium acetate buffer and weigh the tube once more (this will be the total mass of the liquid). Record all measurements. Vortex the tube containing the working dilution thoroughly.

Calculation of the Working Dilution Factor: Take the mass of the added 1:100 diluted extract (approximately 1.0 g) and divide it by the total mass of liquid in the tube (approximately 5.0 g). The inverse of this value is the working dilution factor. It will be approximately 5 based upon mass. The total dilution is 1:500 (1:100 dilution×1:5 dilution). The dilutions described here are in the table 5 below.

TABLE 6

Dilutions.

| Primary Dilution (1:10 Final) | | Secondary Dilution (1:100 Final) | | Working dilution (1:500 Final) | |
|---|---|---|---|---|---|
| 0.5 ml 1× Extract | 4.5 ml 250 mM Sodium Acetate Buffer | 0.5 ml 1:10 Diluted Extract | 4.5 ml 250 mM Sodium Acetate Buffer | 1.0 ml 1:100 Diluted Extract | 4.0 ml 250 mM Sodium Acetate Buffer |

* The working dilution will vary depending on the expected activity of the corn phytase dry product. This example is for an expected activity of 1,000 U/g. If a working dilution other than 1:500 is required to get the assay on scale, adjust the ratio of secondary dilution material to the 250 mM sodium acetate buffer accordingly. Keep the final volume of each working dilution at 5 mL.

Preparation of Phosphate Standard Curve Samples Use the 7.2 mM standard potassium phosphate solution prepared as above to make up the following phosphate standards:

TABLE 7

Phosphate Standard Curve

| Standard | Vol of 250 mM sodium acetate buffer (µL) | Vol of 7.2 mM Pi (µL) | Phosphate (µmols) |
|---|---|---|---|
| 1 | 500.0 | 0.0 | 0.000 |
| 2 | 450.0 | 50.0 | 0.360 |
| 3 | 425.0 | 75.0 | 0.540 |
| 4 | 400.0 | 100.0 | 0.720 |
| 5 | 375.0 | 125.0 | 0.900 |
| 6 | 350.0 | 150.0 | 1.080 |
| 7 | 300.0 | 200.0 | 1.440 |

Aliquot the phosphate/buffer volumes listed in the table above into test tubes. Add 1.0 mL of substrate to each standard tube and vortex to mix. Add 1.0 mL of color top solution to the standards following the assay, and mix. Upon the addition of all of the reagents the final volume of each standard curve sample will be 2.5 mL. The phosphate standard curve samples do not need to be incubated at 37° C. for the 60 minutes. A phosphate standard curve must be prepared each time a set of assays is performed, but does not need to be conducted in duplicate, as variations in the standard curve are minimal from assay to assay. The concentration range of the phosphate standard curve is such that standard 7 will produce an absorbance of approximately 1.1 to 1.2 at 415 nm. Assay sample absorbances should not go above this higher limit value. If so dilute the test enzyme samples further and repeat the assay.

Phytase Enzyme Assay Aliquot 1.0 mL of sodium phytate substrate into 16×100 mm glass test tubes and pre-incubate for 5 minutes at 37° C. (see summary of sample/reagent additions below). Prepare three test tubes for the enzyme reactions and three for the reaction blanks for each enzyme sample (6 substrate tubes total per enzyme replicate). The use of screw-capped test tubes is not necessary as evaporation during the course of the reaction is negligible.

Pre-incubate the 5 mL working dilution enzyme samples for 5 minutes 37° C. This 5 minute incubation period equilibrates the substrate and enzyme to the appropriate temperature prior to reaction initiation.

Following the 5 minutes of pre-incubation add 0.5 mL of working dilution sample to the first of the six 1.0 mL sodium phytate substrate tubes. Start a timer upon the addition of diluted enzyme to the first tube. Continue adding diluted enzyme sample to the second and third sodium phytate substrate tubes at a constant rate (i.e. addition of diluted enzyme to a tube every 5 seconds), but do not add diluted enzyme to the three blank tubes at this stage in the assay. The constant enzyme addition rate established during this portion of the assay will be required again during the reaction quenching protocol. Subsequent to the addition of the last aliquot of diluted enzyme vortex all reaction tubes and quickly return them to the 37° C. water bath. Incubate for 60 minutes.

Following the 60 minute incubation period add 1.0 mL of color stop solution to each enzyme reaction test tube and also to each blank tube using the constant sample addition rate established above. The use of a constant addition rate will ensure that each sample undergoes 60 minutes of reaction time. Vortex to mix all quenched test tubes.

After the three blank reaction tubes have been quenched with color stop solution add 0.5 mL of diluted enzyme sample to each.

Add 1.0 mL of the color stop solution to each of the 7 phosphate standard curve samples. All reaction, blank, and phosphate standard samples tubes will now contain 2.5 mL of solution. Subsequent to the addition of color stop reagent to all test tubes vortex samples one additional time to ensure complete mixing of reagents, and centrifuge at 2000 g for 10 minutes to clarify samples prior to taking absorbance measurements.

Spectroscopic Measurements and Activity Calculations Using either a plastic (1 cm path length, semi-micro) or a quartz cuvette zero the UV spectrophotometer at 415 nm using dH$_2$O. Read all reaction, blank, and phosphate standard curve samples at 415 nm and record values. Take care not to disturb the precipitated material in the test tubes following centrifugation.

For the 7 phosphate standard curve samples take each UV measurement and subtract the 0 mmol phosphate reading (phosphate standard 1). This corrects all of the phosphate standard curve readings by subtracting a reagent blank. Plot the absorbance at 415 nm as a function of phosphate amount, and then calculate the "best fit" line through the data set using a linear regression program.

For the enzyme reaction samples take the average of the three readings (these should be within 5% of one another and ideally fall into the absorbance range from 0.4 to 1.1) and subtract the average of the three background readings.

Take the background corrected absorbance for each replicate and interpolate using the phosphate standard curve regression parameters. The interpolated value is calculated in units of µmols.

Divide each interpolated µmols value by 60 minutes for the time of reaction and by the mass (in grams) of a 0.5 mL aliquot of 250 mM sodium acetate buffer as determined. The units of this calculation are in µmols/min/g or in phytase units per gram (FTU/g) by definition.

Take the FTU/g value and multiply it by the dilution factor used to get the sample readings on scale. The dilution factor is the product of the primary, secondary and assay working dilutions determined above, respectively.

Multiply the dilution adjusted FTU/g value calculated by the total mass of buffer that was used in the phytase extraction procedure, and then divide that value by the amount of dry material used in the extraction. The mass of the extraction buffer and the amount of dry material extracted should be approximately 100 g and 1.0 g, respectively. The final calculated activity is a mass based activity that is represented in phytase units per gram of dry Quantum phytase product (FTU/g).

Figure 8:
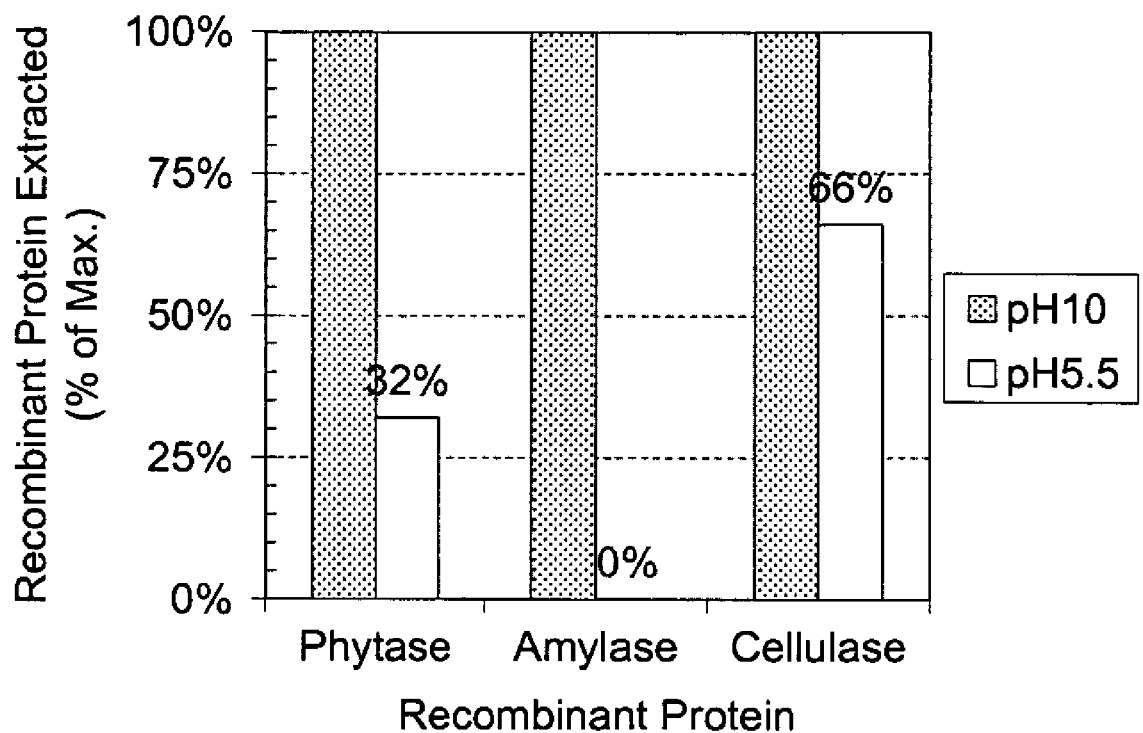
FIG. 8 is a graph showing more efficient extraction of three recombinant enzymes expressed in transgenic corn seed using borate pH 10 buffer compared to sodium acetate pH 5.5 buffer. Five replicate samples of milled transgenic corn seed were extracted at pH 10 (25 mM sodium borate pH 10, 0.01% TWEEN 20) and pH 5.5 (250 mM sodium acetate, 0.01% TWEEN 20). Extracts were diluted and analyzed by ELISA. The relative amount of the recombinant enzyme protein extracted at pH 5.5 is compared to the amount of the protein extracted using borate pH 10 buffer.

This assay method for corn phytase was performed and the results are set forth in FIGS. 7 and 8. This extraction method worked sufficiently for samples of feed made with transgenic corn expressing a phytase enzyme.

While the present invention has been described with reference to specific embodiments thereof, it will be appreciated that numerous variations, modifications, and further embodiments are possible, and accordingly, all such variations, modifications and embodiments are to be regarded as being within the scope of the present invention. Numerous patents, applications and references are discussed or cited within this specification, and all are incorporated by reference in their entireties.

What is claimed is:

1. A method for extracting and measuring phytase activity in feed, comprising the steps of:
    a) grinding a feed sample of at least about 300 grams±30 grams so that about 80% of the material has a particle size of 250 pm or less to make a ground feed sample;
    b) mixing the ground feed sample with an aqueous borate buffer of about 25 mM sodium borate at about pH 10.0±polysorbate 20 at about 0.01%;
    c) extracting the phytase from the ground feed sample, while significantly reducing extraction of background phosphate from feed as compared to extraction at pH 8.0 or lower; and
    d) measuring the phytase activity.

2. The method of claim 1, wherein the phytase is an *E. coli* phytase or a phytase derived from *E. coli*.

3. The method of claim 1, wherein the phytase is thermostable.

4. The method of claim 1, wherein the feed sample is a mash or pelleted feed sample.

5. The method of claim 1, wherein the feed phytase was produced in a transgenic plant.

6. The method of claim 1, wherein the feed is pelleted feed.

7. The method of claim 6, wherein the method for measuring phytase activity comprises a constant coefficient of variation (CV) of less than 10% across replicate extractions.

8. The method of claim 1, wherein the method for measuring phytase activity comprises a constant coefficient of variation (CV) of less than 10% across replicate extractions.

9. The method of claim 1, wherein the feed is conditioned at a temperature of 70° C. to 83° C.

10. The method of claim 1, wherein the aqueous borate buffer comprises about 25 mM sodium borate at about pH 10.0, with polysorbate 20.

11. The method of claim 1, wherein the aqueous borate buffer comprises about 25 mM sodium borate at about pH 10.0, without polysorbate 20.

* * * * *